(12) United States Patent
Hariton et al.

(10) Patent No.: US 11,648,111 B2
(45) Date of Patent: *May 16, 2023

(54) LOW PROFILE TRANSCATHETER HEART VALVE

(71) Applicant: Edwards Lifesciences Corporation, Irvine, CA (US)

(72) Inventors: Ilia Hariton, Zichron Yaacov (IL); Netanel Benichou, D.n. Hof Hacarmel (IL); Yaacov Nitzan, Hertzeliya (IL); Bella Felsen, Hiafa (IL); Diana Nguyen-Thien-Nhon, Irvine, CA (US); Rajesh A. Khanna, Aliso Viejo, CA (US); Son V. Nguyen, Irvine, CA (US); Tamir S. Levi, Zikhron Yaakov (IL); Itai Pelled, Ramat-Hasharon (IL)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/558,322

(22) Filed: Dec. 21, 2021

(65) Prior Publication Data

US 2022/0110749 A1 Apr. 14, 2022

Related U.S. Application Data

(60) Continuation of application No. 16/570,780, filed on Sep. 13, 2019, now Pat. No. 11,213,388, which is a
(Continued)

(51) Int. Cl.
*A61F 2/24* (2006.01)
*A61F 2/95* (2013.01)
(Continued)

(52) U.S. Cl.
CPC .......... *A61F 2/2418* (2013.01); *A61F 2/2412* (2013.01); *A61F 2/2433* (2013.01);
(Continued)

(58) Field of Classification Search
CPC ........ A61F 2/24; A61F 2/2412; A61F 2/2418; A61F 2/2433
(Continued)

(56) References Cited

U.S. PATENT DOCUMENTS 3,409,013 A 11/1968 Berry
3,534,411 A 10/1970 Shiley
(Continued)

FOREIGN PATENT DOCUMENTS

DE 2246526 A1 3/1973
DE 19532846 A1 3/1997
(Continued)

OTHER PUBLICATIONS

Andersen, et al., Transluminal implantation of artificial heart valves. Description of a new expandable aortic valve and initial results withimplantation by catheter technique in closed chest pigs. European Heart Journal (1992), 13, 704-708.
(Continued)

*Primary Examiner* — Suzette J Gherbi
(74) *Attorney, Agent, or Firm* — Klarquist Sparkman, LLP; Joel B. German

(57) ABSTRACT

An implantable prosthetic valve includes a radially collapsible and expandable annular frame having three commissure attachment posts and four rows of circumferential struts. The rows include a first row, a second row downstream of the first row, a third row downstream of the second row, and a fourth row downstream of the third row and defining an outflow end of the frame. Each row of circumferential struts includes angled struts arranged in a zig-zag pattern. A leaflet
(Continued)

structure includes three leaflets forming three commissures, each commissure being connected to one of the commissure attachment posts only at locations along the commissure attachment posts between a first plane that is perpendicular to a longitudinal axis of the frame and intersects crowns of the third row of struts and a second plane that is perpendicular to the longitudinal axis and intersects crowns of the fourth row of struts.

24 Claims, 15 Drawing Sheets

Related U.S. Application Data continuation of application No. 16/202,980, filed on Nov. 28, 2018, now Pat. No. 10,426,611, which is a continuation of application No. 15/984,716, filed on May 21, 2018, now Pat. No. 10,492,905, which is a continuation of application No. 15/599,802, filed on May 19, 2017, now Pat. No. 9,974,652, which is a division of application No. 14/483,862, filed on Sep. 11, 2014, now Pat. No. 9,662,204, which is a continuation of application No. 13/897,036, filed on May 17, 2013, now abandoned, which is a continuation of application No. 13/167,549, filed on Jun. 23, 2011, now Pat. No. 8,454,685, which is a continuation of application No. 12/480,603, filed on Jun. 8, 2009, now Pat. No. 7,993,394.

(60) Provisional application No. 61/059,656, filed on Jun. 6, 2008.

(51) Int. Cl.
*B05B 1/18* (2006.01)
*E03C 1/06* (2006.01)
*E03C 1/02* (2006.01)

(52) U.S. Cl.
CPC .............. *A61F 2/2475* (2013.01); *A61F 2/95* (2013.01); *B05B 1/185* (2013.01); *E03C 1/025* (2013.01); *E03C 1/066* (2013.01); *A61F 2/9522* (2020.05); *A61F 2220/005* (2013.01); *A61F 2220/0033* (2013.01); *A61F 2220/0075* (2013.01); *A61F 2230/0054* (2013.01); *Y10T 29/49863* (2015.01)

(58) Field of Classification Search
USPC .................................................. 623/2.1–2.19
See application file for complete search history.

(56) References Cited

U.S. PATENT DOCUMENTS

| | | | |
|---|---|---|---|
| 3,548,417 A | 12/1970 | Kisher | |
| 3,551,913 A | 1/1971 | Shiley et al. | |
| 3,570,014 A | 3/1971 | Hancock | |
| 3,587,115 A | 6/1971 | Shiley | |
| 3,608,097 A | 9/1971 | Bellhouse | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,818,511 A | 6/1974 | Goldberg et al. | |
| 3,848,578 A | 11/1974 | Bucalo | |
| 3,983,581 A | 10/1976 | Angell et al. | |
| 4,035,849 A | 7/1977 | Angell et al. | |
| 4,056,854 A | 11/1977 | Boretos et al. | |
| 4,084,268 A | 4/1978 | Ionescu et al. | |
| 4,106,129 A | 8/1978 | Carpentier et al. | |
| 4,173,606 A * | 11/1979 | Stoy | B29C 39/00 264/237 |
| 4,192,020 A | 3/1980 | Davis et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,477,930 A | 10/1984 | Totten et al. | |
| 4,501,030 A | 2/1985 | Lane | |
| 4,506,394 A | 3/1985 | Bedard | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,662,890 A | 5/1987 | Burton | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,139,515 A | 8/1992 | Robicsek | |
| 5,147,399 A | 9/1992 | Dellon et al. | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,425,739 A | 6/1995 | Jessen | |
| 5,443,446 A | 8/1995 | Shturman | |
| 5,469,868 A | 11/1995 | Reger | |
| 5,476,506 A | 12/1995 | Lunn | |
| 5,480,424 A | 1/1996 | Cox | |
| 5,489,297 A | 2/1996 | Duran | |
| 5,500,014 A | 3/1996 | Quijano et al. | |
| 5,522,881 A | 6/1996 | Lentz | |
| 5,545,209 A | 8/1996 | Roberts et al. | |
| 5,545,214 A | 8/1996 | Stevens | |
| 5,549,665 A | 8/1996 | Vesely et al. | |

(56) References Cited

U.S. PATENT DOCUMENTS

| | | | |
|---|---|---|---|
| 5,554,185 | A | 9/1996 | Block et al. |
| 5,558,644 | A | 9/1996 | Boyd et al. |
| 5,562,727 | A | 10/1996 | Turk et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,784 | A | 5/1997 | Strecker |
| 5,628,792 | A | 5/1997 | Lentell |
| 5,639,274 | A | 6/1997 | Fischell et al. |
| 5,665,115 | A | 9/1997 | Cragg |
| 5,665,117 | A | 9/1997 | Rhodes |
| 5,681,345 | A | 10/1997 | Euteneuer |
| 5,713,953 | A | 2/1998 | Vallana et al. |
| 5,716,417 | A | 2/1998 | Girard et al. |
| 5,728,068 | A | 3/1998 | Leone et al. |
| 5,741,324 | A | 4/1998 | Glastra |
| 5,741,331 | A * | 4/1998 | Pinchuk ............... B29C 41/08 607/2 |
| 5,749,890 | A | 5/1998 | Shaknovich |
| 5,756,476 | A | 5/1998 | Epstein et al. |
| 5,769,812 | A | 6/1998 | Stevens et al. |
| 5,769,882 | A | 6/1998 | Fogarty et al. |
| 5,800,508 | A | 9/1998 | Goicoechea et al. |
| 5,840,081 | A | 11/1998 | Andersen et al. |
| 5,843,158 | A | 12/1998 | Lenker et al. |
| 5,843,160 | A | 12/1998 | Rhodes |
| 5,853,419 | A | 12/1998 | Imran |
| 5,855,597 | A | 1/1999 | Jayaraman |
| 5,855,601 | A | 1/1999 | Bessler et al. |
| 5,855,602 | A | 1/1999 | Angell |
| 5,891,195 | A | 4/1999 | Klostermeyer et al. |
| 5,910,170 | A | 6/1999 | Reimink et al. |
| 5,925,063 | A | 7/1999 | Khosravi |
| 5,944,750 | A | 8/1999 | Tanner et al. |
| 5,948,191 | A | 9/1999 | Solovay |
| 5,957,949 | A | 9/1999 | Leonhardt et al. |
| 6,010,529 | A | 1/2000 | Herweck et al. |
| 6,015,431 | A | 1/2000 | Thornton et al. |
| 6,027,525 | A | 2/2000 | Suh et al. |
| 6,056,762 | A | 5/2000 | Nash et al. |
| 6,096,071 | A | 8/2000 | Yadav |
| 6,132,473 | A | 10/2000 | Williams et al. |
| 6,159,656 | A | 12/2000 | Kawabe et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,254,636 | B1 | 7/2001 | Peredo |
| 6,258,120 | B1 | 7/2001 | McKenzie et al. |
| 6,273,917 | B1 | 8/2001 | Inoue |
| 6,287,335 | B1 | 9/2001 | Drasler et al. |
| 6,299,637 | B1 | 10/2001 | Shaolian et al. |
| 6,299,638 | B1 | 10/2001 | Sauter |
| 6,302,906 | B1 | 10/2001 | Goecoechea et al. |
| 6,306,163 | B1 | 10/2001 | Fitz |
| 6,309,417 | B1 | 10/2001 | Spence et al. |
| 6,331,188 | B1 | 12/2001 | Lau et al. |
| 6,350,277 | B1 | 2/2002 | Kocur |
| 6,371,983 | B1 | 4/2002 | Lane |
| 6,395,019 | B2 | 5/2002 | Chobotov |
| 6,425,916 | B1 | 7/2002 | Garrison et al. |
| 6,440,164 | B1 | 8/2002 | Di Matteo et al. |
| 6,454,799 | B1 | 9/2002 | Schreck |
| 6,458,153 | B1 | 10/2002 | Bailey et al. |
| 6,458,156 | B1 | 10/2002 | Wan et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,494,909 | B2 | 12/2002 | Greenhalgh |
| 6,503,272 | B2 | 1/2003 | Duerig et al. |
| 6,527,979 | B2 | 3/2003 | Constantz |
| 6,551,350 | B1 | 4/2003 | Thornton et al. |
| 6,569,196 | B1 | 5/2003 | Vesely |
| 6,582,462 | B1 | 6/2003 | Andersen et al. |
| 6,585,761 | B2 | 7/2003 | Taheri |
| 6,605,112 | B1 | 8/2003 | Moll et al. |
| 6,652,578 | B2 | 11/2003 | Bailey et al. |
| 6,673,285 | B2 * | 1/2004 | Ma .................. B29C 67/202 29/527.1 |
| 6,716,244 | B2 | 4/2004 | Klaco |
| 6,719,781 | B1 | 4/2004 | Kim |
| 6,730,118 | B2 | 5/2004 | Spenser et al. |
| 6,733,525 | B2 | 5/2004 | Yang et al. |
| 6,767,362 | B2 | 7/2004 | Schreck |
| 6,770,579 | B1 * | 8/2004 | Dawson ................ A41D 31/02 428/137 |
| 6,773,456 | B1 | 8/2004 | Gordon et al. |
| 6,830,584 | B1 | 12/2004 | Seguin |
| 6,878,162 | B2 | 4/2005 | Bales et al. |
| 6,893,460 | B2 * | 5/2005 | Spenser ............... A61F 2/2418 623/2.14 |
| 6,896,690 | B1 | 5/2005 | Lambrecht et al. |
| 6,908,481 | B2 | 6/2005 | Cribier |
| 6,918,926 | B2 | 7/2005 | Letort |
| 6,936,067 | B2 | 8/2005 | Buchanan |
| 7,018,406 | B2 | 3/2006 | Seguin et al. |
| 7,018,408 | B2 | 3/2006 | Bailey et al. |
| 7,044,962 | B2 | 5/2006 | Elliott |
| 7,083,648 | B2 * | 8/2006 | Yu ...................... A61F 2/60 604/174 |
| 7,090,693 | B1 | 8/2006 | Chobotov et al. |
| 7,220,274 | B1 | 5/2007 | Quinn |
| 7,273,493 | B2 | 9/2007 | Ledergerber |
| 7,276,078 | B2 | 10/2007 | Spenser et al. |
| 7,276,084 | B2 | 10/2007 | Yang et al. |
| 7,318,278 | B2 | 1/2008 | Zhang et al. |
| 7,329,279 | B2 | 2/2008 | Haug et al. |
| 7,374,571 | B2 | 5/2008 | Pease et al. |
| 7,381,219 | B2 | 6/2008 | Salahieh et al. |
| 7,393,360 | B2 | 7/2008 | Spenser et al. |
| 7,445,631 | B2 | 11/2008 | Salahieh et al. |
| 7,462,191 | B2 | 12/2008 | Spenser et al. |
| 7,510,571 | B2 | 3/2009 | Spiridigliozzi et al. |
| 7,510,575 | B2 | 3/2009 | Spenser et al. |
| 7,563,277 | B2 | 7/2009 | Case et al. |
| 7,563,280 | B2 | 7/2009 | Anderson et al. |
| 7,585,321 | B2 | 9/2009 | Cribier |
| 7,615,373 | B2 * | 11/2009 | Simpson ............. A61L 27/3839 623/23.72 |
| 7,618,446 | B2 | 11/2009 | Andersen et al. |
| 7,618,447 | B2 | 11/2009 | Case et al. |
| 7,655,034 | B2 | 2/2010 | Mitchell et al. |
| 7,704,740 | B2 * | 4/2010 | Schindler ............ D01D 5/0007 435/395 |
| 7,748,389 | B2 | 7/2010 | Salahieh et al. |
| 7,780,725 | B2 | 8/2010 | Haug et al. |
| 7,785,366 | B2 | 8/2010 | Maurer et al. |
| 7,824,442 | B2 | 11/2010 | Salahieh et al. |
| 7,824,443 | B2 | 11/2010 | Salahieh et al. |
| 7,862,609 | B2 | 1/2011 | Butaric et al. |
| 7,959,666 | B2 | 6/2011 | Salahieh et al. |
| 7,959,672 | B2 | 6/2011 | Salahieh et al. |
| 7,988,724 | B2 | 8/2011 | Salahieh et al. |
| 7,993,386 | B2 | 8/2011 | Elliott |
| 7,993,394 | B2 * | 8/2011 | Hariton ................ E03C 1/066 623/2.17 |
| 8,029,556 | B2 | 10/2011 | Rowe |
| 8,048,153 | B2 | 11/2011 | Salahieh et al. |
| 8,052,749 | B2 | 11/2011 | Salahieh et al. |
| 8,167,932 | B2 | 5/2012 | Bourang |
| 8,182,528 | B2 | 5/2012 | Salahieh et al. |
| 8,231,670 | B2 | 7/2012 | Salahieh et al. |
| 8,246,678 | B2 | 8/2012 | Salahieh et al. |
| 8,252,052 | B2 | 8/2012 | Salahieh et al. |
| 8,287,584 | B2 | 10/2012 | Salahieh et al. |
| 8,291,570 | B2 | 10/2012 | Eidenschink et al. |

(56) References Cited

U.S. PATENT DOCUMENTS

| | | | |
|---|---|---|---|
| 8,328,868 B2 | 12/2012 | Paul et al. | |
| 8,343,213 B2 | 1/2013 | Salahieh et al. | |
| 8,449,606 B2 | 5/2013 | Eliasen et al. | |
| 8,454,685 B2 * | 6/2013 | Hariton | A61F 2/2418 623/2.17 |
| 8,579,962 B2 | 11/2013 | Salahieh et al. | |
| 8,603,160 B2 | 12/2013 | Salahieh et al. | |
| 8,617,236 B2 | 12/2013 | Paul et al. | |
| 8,623,076 B2 | 1/2014 | Salahieh et al. | |
| 8,623,078 B2 | 1/2014 | Salahieh et al. | |
| 8,668,733 B2 | 3/2014 | Haug et al. | |
| 8,740,974 B2 | 6/2014 | Lambrecht et al. | |
| 8,747,463 B2 | 6/2014 | Fogarty et al. | |
| 8,828,078 B2 | 9/2014 | Salahieh et al. | |
| 8,840,662 B2 | 9/2014 | Salahieh et al. | |
| 8,840,663 B2 | 9/2014 | Salahieh et al. | |
| 8,858,620 B2 | 10/2014 | Salahieh et al. | |
| 8,894,703 B2 | 11/2014 | Salahieh et al. | |
| 8,951,299 B2 | 2/2015 | Paul et al. | |
| 8,961,599 B2 * | 2/2015 | Bruchman | A61F 2/2415 623/2.12 |
| 8,992,608 B2 | 3/2015 | Haug et al. | |
| 9,005,273 B2 | 4/2015 | Salahieh et al. | |
| 9,011,521 B2 | 4/2015 | Haug et al. | |
| 9,277,991 B2 | 3/2016 | Salahieh et al. | |
| 9,308,085 B2 | 4/2016 | Salahieh et al. | |
| 9,320,599 B2 | 4/2016 | Salahieh et al. | |
| 9,554,900 B2 * | 1/2017 | Bruchman | A61L 27/26 |
| 9,662,204 B2 * | 5/2017 | Hariton | A61F 2/2475 |
| 9,974,652 B2 * | 5/2018 | Hariton | E03C 1/066 |
| 10,292,817 B2 * | 5/2019 | Hariton | A61F 2/2475 |
| 10,413,407 B2 * | 9/2019 | Hariton | A61F 2/2433 |
| 10,426,611 B2 * | 10/2019 | Hariton | E03C 1/266 |
| 10,470,878 B2 * | 11/2019 | Bruchman | A61L 27/26 |
| 10,492,905 B2 * | 12/2019 | Hariton | E03C 1/025 |
| 11,213,388 B2 * | 1/2022 | Hariton | A61F 2/2433 |
| 2001/0021872 A1 | 9/2001 | Bailey et al. | |
| 2001/0027338 A1 | 10/2001 | Greenberg | |
| 2001/0037142 A1 | 11/2001 | Stelter et al. | |
| 2002/0026094 A1 | 2/2002 | Roth | |
| 2002/0032481 A1 | 3/2002 | Gabbay | |
| 2002/0052643 A1 | 5/2002 | Wholey et al. | |
| 2002/0058987 A1 | 5/2002 | Butaric et al. | |
| 2002/0138135 A1 | 9/2002 | Duerig et al. | |
| 2002/0173842 A1 | 11/2002 | Buchanan | |
| 2003/0009211 A1 | 1/2003 | DiCarlo | |
| 2003/0012905 A1 * | 1/2003 | Zumbrum | B23B 25/08 428/422 |
| 2003/0050694 A1 | 3/2003 | Yang et al. | |
| 2003/0100939 A1 | 5/2003 | Yodfat et al. | |
| 2003/0120331 A1 | 6/2003 | Chobotov et al. | |
| 2003/0125797 A1 | 7/2003 | Chobotov et al. | |
| 2003/0130729 A1 | 7/2003 | Paniagua et al. | |
| 2003/0158597 A1 | 8/2003 | Quiachon et al. | |
| 2003/0167089 A1 | 9/2003 | Lane | |
| 2003/0212450 A1 | 11/2003 | Schlick | |
| 2003/0212454 A1 | 11/2003 | Scott et al. | |
| 2003/0216803 A1 | 11/2003 | Ledergerber | |
| 2003/0236567 A1 | 12/2003 | Elliot | |
| 2004/0039436 A1 | 2/2004 | Spenser et al. | |
| 2004/0082989 A1 | 4/2004 | Cook et al. | |
| 2004/0093060 A1 | 5/2004 | Seguin et al. | |
| 2004/0186563 A1 | 9/2004 | Iobbi | |
| 2004/0186565 A1 | 9/2004 | Schreck | |
| 2004/0260389 A1 | 12/2004 | Case et al. | |
| 2005/0075728 A1 | 4/2005 | Nguyen et al. | |
| 2005/0096736 A1 | 5/2005 | Osse et al. | |
| 2005/0131518 A1 | 6/2005 | Hartley et al. | |
| 2005/0137688 A1 | 6/2005 | Salahieh et al. | |
| 2005/0159811 A1 | 7/2005 | Lane | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0149350 A1 | 7/2006 | Patel et al. | |
| 2006/0149360 A1 | 7/2006 | Schwammenthal et al. | |
| 2006/0183383 A1 | 8/2006 | Asmus et al. | |
| 2006/0195172 A1 | 8/2006 | Luo et al. | |
| 2006/0224228 A1 | 10/2006 | Dehdashtian et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0287717 A1 | 12/2006 | Rowe et al. | |
| 2007/0005131 A1 | 1/2007 | Taylor | |
| 2007/0010877 A1 | 1/2007 | Salahieh et al. | |
| 2007/0088425 A1 | 4/2007 | Schaeffer | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0275537 A1 | 11/2008 | Limon | |
| 2009/0004239 A1 * | 1/2009 | Ladet | A61L 27/48 424/423 |
| 2009/0125118 A1 | 5/2009 | Gong | |
| 2009/0157175 A1 | 6/2009 | Benichou | |
| 2009/0187197 A1 * | 7/2009 | Roeber | D04B 21/12 606/151 |
| 2009/0276040 A1 | 11/2009 | Rowe et al. | |
| 2009/0281619 A1 | 11/2009 | Le et al. | |
| 2009/0299452 A1 | 12/2009 | Eidenschink et al. | |
| 2009/0319037 A1 | 12/2009 | Rowe et al. | |
| 2010/0049313 A1 | 2/2010 | Alon et al. | |
| 2010/0190254 A1 * | 7/2010 | Chian | D01D 5/0076 156/60 |
| 2010/0198347 A1 | 8/2010 | Zakay et al. | |
| 2010/0204781 A1 | 8/2010 | Alkhatib | |
| 2010/0249922 A1 * | 9/2010 | Li | A61F 2/2412 623/2.12 |
| 2010/0297768 A1 * | 11/2010 | Schindler | C12M 25/14 252/301.16 |
| 2011/0015729 A1 | 1/2011 | Jimenez et al. | |
| 2011/0039690 A1 * | 2/2011 | Niu | B01D 39/2065 252/502 |
| 2011/0142804 A1 * | 6/2011 | Gaudette | C12N 5/0068 435/177 |
| 2011/0218620 A1 | 9/2011 | Meiri et al. | |
| 2011/0250689 A1 * | 10/2011 | Baaijens | D04H 1/43838 428/364 |
| 2011/0311746 A1 * | 12/2011 | Ma | A61L 27/56 264/28 |
| 2011/0319991 A1 | 12/2011 | Hariton et al. | |
| 2012/0058100 A1 * | 3/2012 | Shastri | A61K 47/34 424/94.4 |
| 2012/0061314 A1 * | 3/2012 | Choi | B01D 67/0088 210/490 |
| 2012/0123529 A1 | 5/2012 | Levi et al. | |
| 2012/0129150 A1 * | 5/2012 | Carbonell | B01J 20/328 210/500.1 |
| 2012/0253453 A1 * | 10/2012 | Bruchman | A61F 2/2418 623/1.24 |
| 2012/0296418 A1 * | 11/2012 | Bonyuet | A61F 2/2415 623/2.18 |
| 2012/0323315 A1 * | 12/2012 | Bruchman | A61L 27/507 623/2.12 |
| 2013/0023985 A1 | 1/2013 | Khairkhahan et al. | |
| 2013/0150947 A1 * | 6/2013 | Kaufmann | A61L 27/54 623/1.15 |
| 2013/0268044 A1 | 10/2013 | Parsons et al. | |
| 2013/0310924 A1 * | 11/2013 | Groothuis | A61F 2/2436 623/2.11 |
| 2013/0310926 A1 | 11/2013 | Hariton | |

(56) References Cited

U.S. PATENT DOCUMENTS

| | | |
|---|---|---|
| 2013/0317598 A1 | 11/2013 | Rowe et al. |
| 2014/0209238 A1 | 7/2014 | Bonyuet et al. |
| 2014/0288642 A1* | 9/2014 | Yoshida ............... A61L 27/24 623/2.17 |
| 2015/0224231 A1* | 8/2015 | Bruchman ........... A61L 2/2418 156/70 |
| 2015/0257875 A1* | 9/2015 | Bruchman ............. A61L 27/48 623/2.12 |
| 2015/0257876 A1* | 9/2015 | Bruchman ............. A61L 27/34 623/2.17 |
| 2015/0265744 A1* | 9/2015 | Baaijens ............... A61L 27/56 435/396 |
| 2015/0283297 A1* | 10/2015 | Baaijens ........... D04H 1/43838 435/396 |
| 2015/0305862 A1* | 10/2015 | Bruchman ............ A61F 2/2412 156/185 |
| 2015/0306277 A1* | 10/2015 | Pathak ................ A61L 27/3612 424/443 |
| 2015/0366663 A1* | 12/2015 | Bruchman ............ A61F 2/2409 623/2.19 |
| 2016/0008133 A9* | 1/2016 | Day ......................... A61F 2/28 427/2.27 |
| 2016/0067374 A1* | 3/2016 | Puckett ................. D04H 1/558 442/350 |
| 2016/0074161 A1* | 3/2016 | Bennett ................ A61F 2/2412 29/890.126 |
| 2016/0100939 A1* | 4/2016 | Armstrong ............ A61F 2/2415 623/2.12 |
| 2016/0175095 A1* | 6/2016 | Dienno ................. A61F 2/2415 623/2.17 |
| 2016/0175096 A1* | 6/2016 | Dienno ................. A61F 2/2415 623/2.13 |
| 2018/0263769 A1 | 9/2018 | Hariton et al. |
| 2019/0091018 A1 | 3/2019 | Hariton et al. |
| 2019/0099268 A1 | 4/2019 | Hariton et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0144167 A2 | 6/1985 |
| EP | 0597967 A1 | 5/1994 |
| EP | 0592410 B1 | 10/1995 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 A2 | 6/2007 |
| EP | 3476367 A1 | 5/2019 |
| EP | 3501455 A1 | 6/2019 |
| EP | 3476367 B1 | 12/2019 |
| EP | 3501455 B1 | 12/2019 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9822159 A2 | 5/1998 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9944540 A2 | 9/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0166035 A2 | 9/2001 |
| WO | 0176510 A2 | 10/2001 |
| WO | 0222054 A1 | 3/2002 |
| WO | 0241789 A2 | 5/2002 |
| WO | 05236048 A1 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005084595 A1 | 9/2005 |
| WO | 2006014233 A2 | 2/2006 |
| WO | 2006034008 A2 | 3/2006 |
| WO | 2006070372 A2 | 7/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2007103229 A2 | 9/2007 |
| WO | 2008005405 A2 | 1/2008 |
| WO | 2008011261 A2 | 1/2008 |
| WO | 2008035337 A2 | 3/2008 |
| WO | 2008070244 A2 | 6/2008 |
| WO | 2008079962 A1 | 7/2008 |
| WO | 2008091515 A2 | 7/2008 |
| WO | 2008106531 A1 | 9/2008 |
| WO | 2008147964 A1 | 12/2008 |
| WO | 2008150529 A1 | 12/2008 |
| WO | 2009029199 A1 | 3/2009 |
| WO | 2009033469 A1 | 3/2009 |
| WO | 2009042196 A2 | 4/2009 |
| WO | 2009052188 A1 | 4/2009 |
| WO | 2009053497 A1 | 4/2009 |
| WO | 2009149462 A2 | 12/2009 |
| WO | 2010121076 A2 | 10/2010 |

OTHER PUBLICATIONS

Andersen, Henning Rud, History of Percutaneous Aortic Valve Prosthesis, Herz 34 2009 Nr. 5, Urban & Vogel, pp. 343-346, Skejby University Hospital Department of Cardiology, Aarhus, Denmark.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

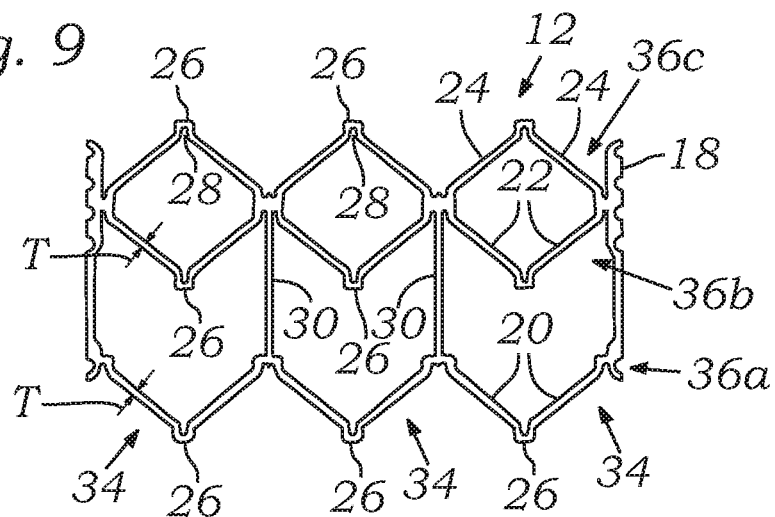
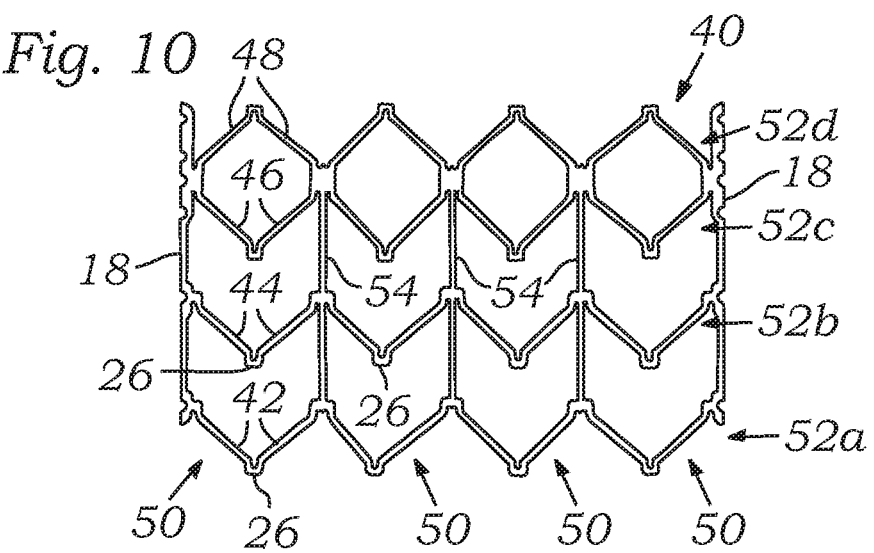
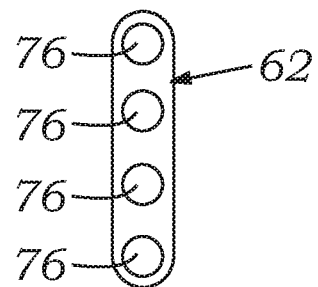

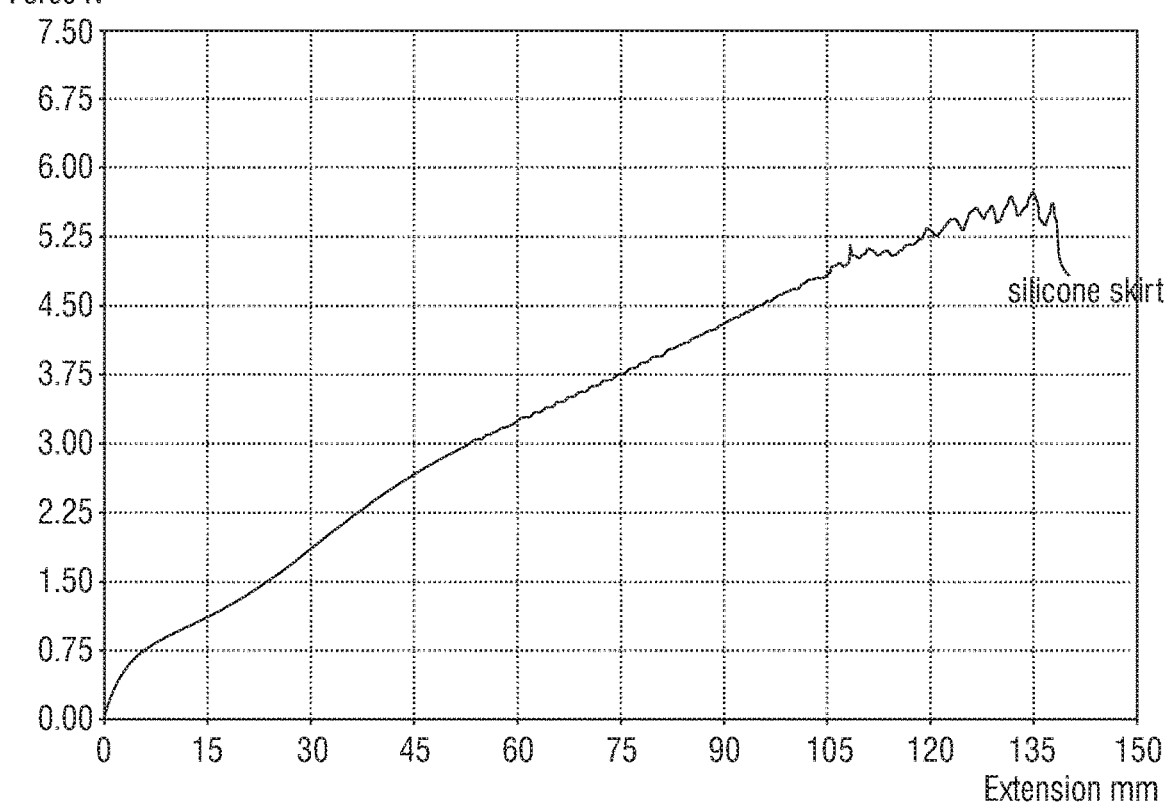
Fig. 31D Cuve for Product silicone skirt8
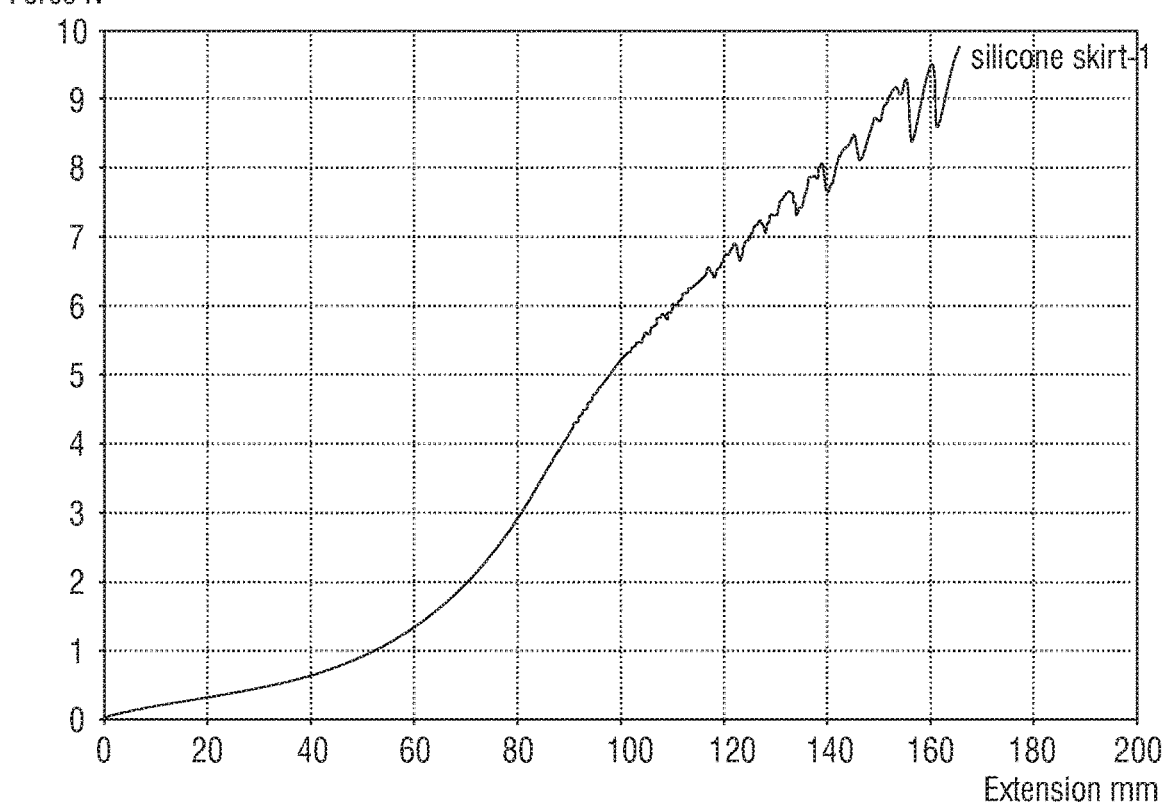
Fig. 31E Cuve for Product silicone skirt7

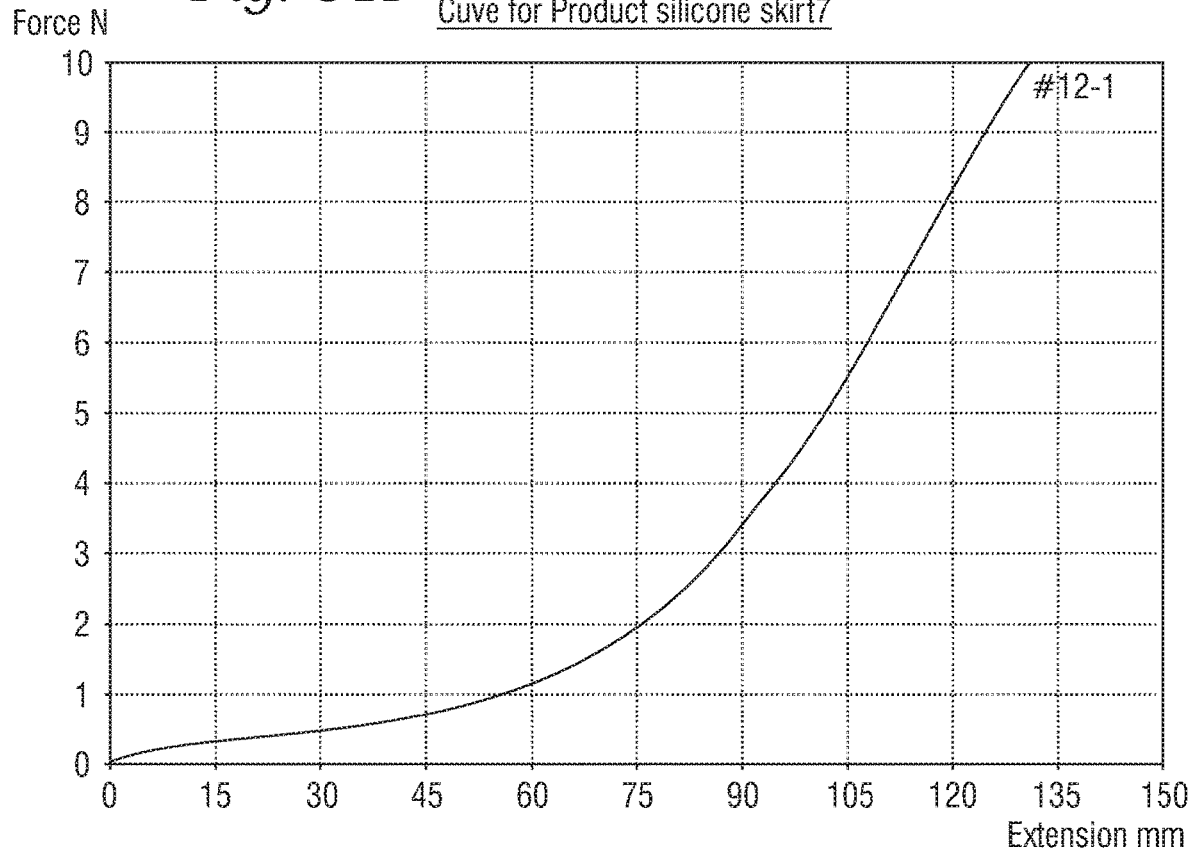

LOW PROFILE TRANSCATHETER HEART VALVE

CROSS REFERENCE TO RELATED APPLICATIONS

This application is a continuation of U.S. patent application Ser. No. 16/570,780, filed Sep. 13, 2019, which is a continuation of U.S. patent application Ser. No. 16/202,980, filed Nov. 28, 2018, now U.S. Pat. No. 10,426,611, which is a continuation of U.S. patent application Ser. No. 15/984,716, filed May 21, 2018, now U.S. Pat. No. 10,492,905, which is a continuation of U.S. patent application Ser. No. 15/599,802, filed May 19, 2017, now U.S. Pat. No. 9,974,652, which is a divisional of U.S. patent application Ser. No. 14/483,862, filed Sep. 11, 2014, now U.S. Pat. No. 9,662,204, which is a continuation of U.S. patent application Ser. No. 13/897,036, filed May 17, 2013, now abandoned, which is a continuation of U.S. patent application Ser. No. 13/167,549, filed Jun. 23, 2011, now U.S. Pat. No. 8,454,685, which is a continuation of U.S. patent application Ser. No. 12/480,603, filed Jun. 8, 2009, now U.S. Pat. No. 7,993,394, which claims the benefit of U.S. Patent Application No. 61/059,656, filed Jun. 6, 2008, the entire disclosures of which are incorporated herein by reference.

FIELD

The present disclosure relates to implantable devices and, more particularly, to valve prosthetics for implantation into body ducts, such as native heart valve annuluses.

DESCRIPTION OF THE RELATED ART

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, more than 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the diameter of the folded or crimped profile. The diameter of the crimped profile is important because it directly influences the physician's ability to advance the valve through the femoral artery or vein. More particularly, a smaller profile allows for treatment of a wider population of patients, with enhanced safety.

SUMMARY

The present disclosure is directed toward new and non-obvious methods and apparatuses relating to prosthetic valves, such as heart valves.

In one representative embodiment, an implantable prosthetic valve comprises a radially collapsible and expandable frame, or stent, and a leaflet structure comprising a plurality of leaflets. The leaflet structure has a scalloped lower edge portion that is positioned inside of and secured to the frame. The valve can further include an annular skirt member, which can be disposed between the frame and the leaflet structure such that the scalloped lower edge portion can be attached to an inner surface of the skirt member. Each leaflet can have an upper edge, a curved lower edge and two side flaps extending between respective ends of the upper edge and the lower edge, wherein each side flap is secured to an adjacent side flap of another leaflet to form commissures of the leaflet structure. Each commissure can be attached to one of the commissure attachment posts, and a reinforcing bar can be positioned against each side flap for reinforcing the attachments between the commissures and the commissure attachment posts.

The frame can comprise a plurality of angularly spaced, axial struts that are interconnected by a plurality of rows of circumferential struts. Each row of circumferential struts desirably includes struts arranged in a zig-zag or saw-tooth pattern extending around the circumference of the frame.

In certain embodiments, at least one row, and preferably all rows, of circumferential struts include pairs of circumferential struts extending between two axial struts. Each strut of the pair has one end connected to a respective axial strut and another end interconnected to an adjacent end of the other strut of the same pair by a crown portion such that a gap exists between the adjacent ends of the struts. The angle between the struts of each pair desirably is between about 90 and 110 degrees, with about 100 degrees being a specific example. The frame desirably is made of a nickel-cobalt based alloy, such as a nickel cobalt chromium molybdenum alloy (e.g., MP35N™)

In another representative embodiment, an implantable prosthetic valve comprises a radially collapsible and expandable annular frame and a leaflet structure supported by the frame. The frame can comprise a plurality of interconnected struts defining a plurality of open cells in the frame. The valve further includes an annular cover member disposed on and covering the cells of at least a portion of the frame. The cover member desirably comprises an elastomer, such as silicon, that can expand and stretch when the valve is expanded from a crimped state to an expanded state.

The cover member may be a thin sleeve of silicon that surrounds at least a portion of the frame. Alternatively, the cover member may be formed by dipping at least a portion of the frame in silicon or another suitable elastomer in liquefied form.

In another representative embodiment, a method is disclosed for crimping an implantable prosthetic valve having a frame and leaflets supported by the frame. The method comprises placing the valve in the crimping aperture of a crimping device such that a compressible material is disposed between the crimping jaws of the crimping device and the frame of the valve. Pressure is applied against the compressible material and the valve with the crimping jaws to radially crimp the valve to a smaller profile and compress the compressible material against the valve such that the compressible material extends into open cells of the frame and pushes the leaflets away from the inside of the frame.

The foregoing and other features and advantages of the invention will become more apparent from the following detailed description, which proceeds with reference to the accompanying figures.

BRIEF DESCRIPTION OF THE DRAWINGS

FIG. 9 is a flattened view of 120-degree segment of the frame shown in FIG. 7.

FIG. 10 is a flattened view of 120-degree segment of the frame shown in FIG. 8.

FIG. 11 is a front view of a reinforcing bar that can be used to reinforce the connection of the valve leaflets to a frame in a prosthetic valve such as shown in FIG. 1.

FIGS. 31A-31F are graphs illustrating the results of respective uniaxial tests performed on respective silicon test strips having deliberately introduced tears.

DETAILED DESCRIPTION

Figure 1:
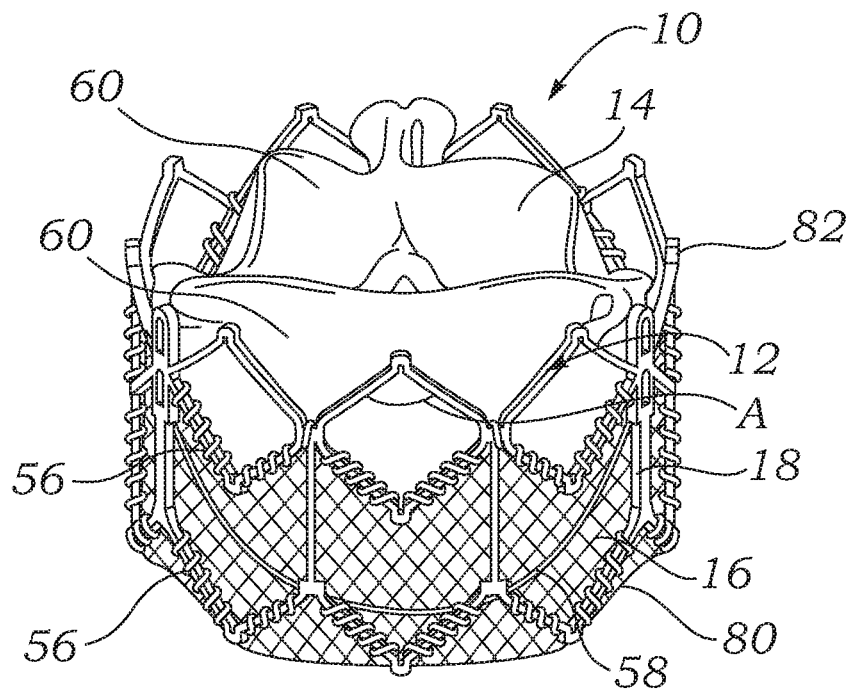
FIG. 1 is a perspective view of a representative embodiment of a prosthetic heart valve.
Figure 2:
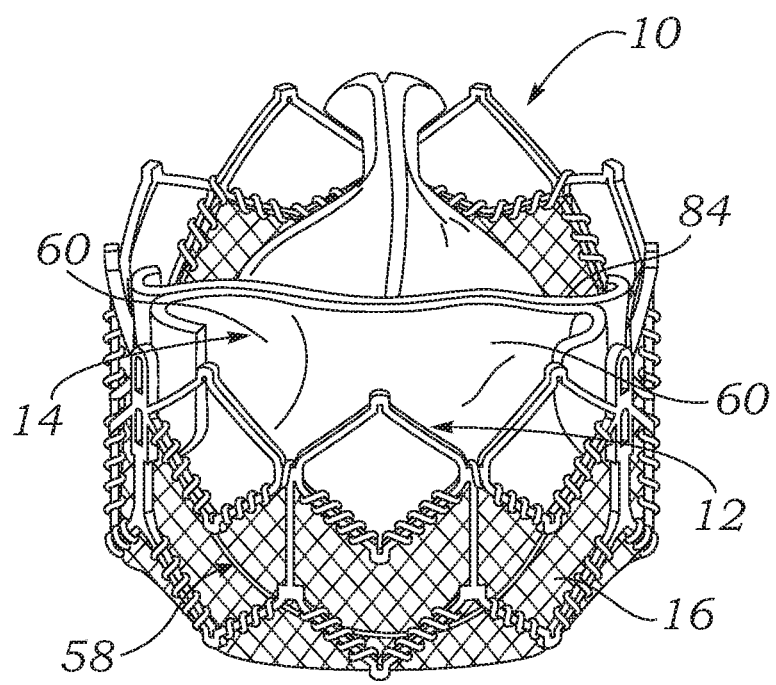
FIG. 2 is another perspective view of the prosthetic valve of FIG. 1.
Figure 3:
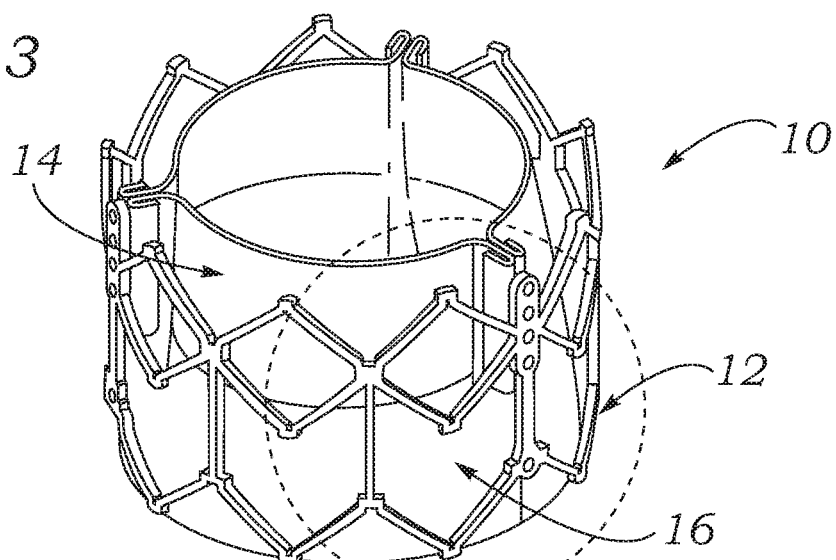
FIG. 3 is another perspective view of the prosthetic valve of FIG. 1.
Figure 4:
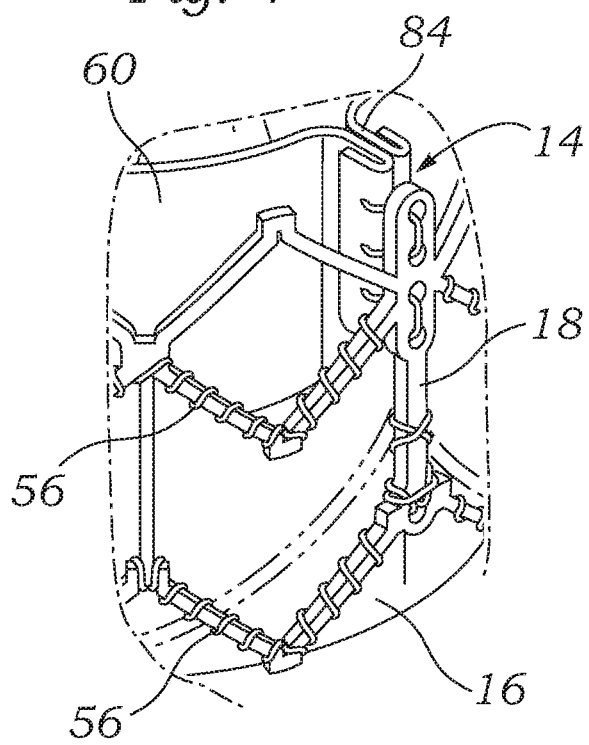
FIG. 4 is an enlarged view of a section of the valve shown in FIG. 3.

FIGS. 1 and 2 illustrate an implantable prosthetic valve 10, according to one embodiment. Valve 10 in the illustrated embodiment generally comprises a frame, or stent, 12, a leaflet structure 14 supported by the frame, and a skirt 16 secured to the outer surface of the leaflet structure. Valve 10 typically is implanted in the annulus of the native aortic valve but also can be adapted to be implanted in other native valves of the heart or in various other ducts or orifices of the body. Valve 10 has a "lower" end 80 and an "upper" end 82. In the context of the present application, the terms "lower" and "upper" are used interchangeably with the terms "inflow" and "outflow", respectively. Thus, for example, the lower end 80 of the valve is its inflow end and the upper end 82 of the valve is its outflow end.

Valve 10 and frame 12 are configured to be radially collapsible to a collapsed or crimped state for introduction into the body on a delivery catheter and radially expandable to an expanded state for implanting the valve at a desired location in the body (e.g., the native aortic valve). Frame 12 can be made of a plastically-expandable material that permits crimping of the valve to a smaller profile for delivery and expansion of the valve using an expansion device such as the balloon of a balloon catheter. Exemplary plastically-expandable materials that can be used to form the frame are described below. Alternatively, valve 10 can be a so-called self-expanding valve wherein the frame is made of a self-expanding material such as Nitinol. A self-expanding valve can be crimped to a smaller profile and held in the crimped state with a restraining device such as a sheath covering the valve. When the valve is positioned at or near the target site, the restraining device is removed to allow the valve to self-expand to its expanded, functional size.

Figure 5:
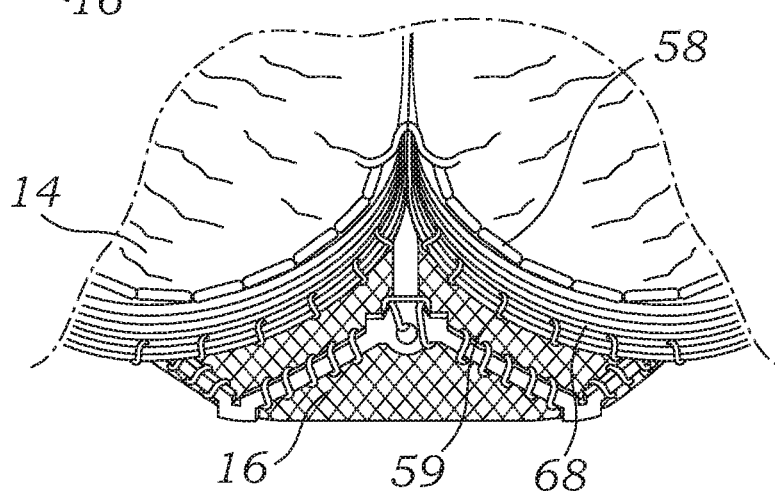
FIG. 5 is a bottom perspective view of the prosthetic valve of FIG. 1 showing the inside of the valve.
Figure 7:
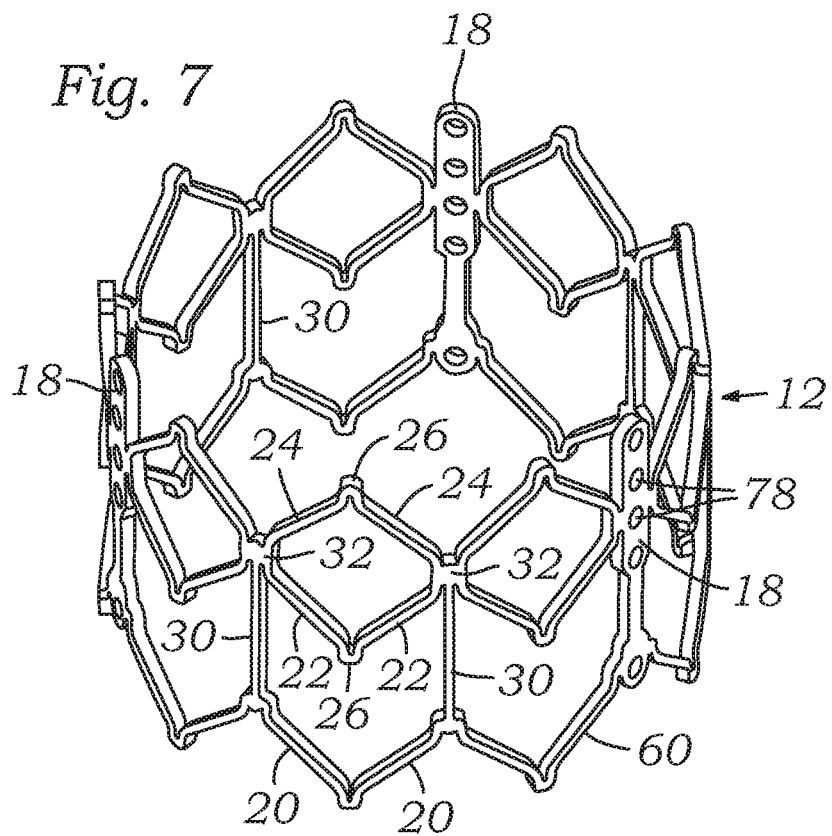
FIG. 7 is a perspective view of the frame of the prosthetic valve of FIG. 1.

Referring also to FIG. 7 (which shows the frame alone for purposes of illustration), frame 12 is an annular, stent-like structure having a plurality of angularly spaced, vertically extending, commissure attachment posts, or struts, 18. Posts 18 can be interconnected via a lower row 36a of circumferentially extending struts 20 and first and second rows upper rows 36b, 36c, respectively, of circumferentially extending struts 22 and 24, respectively. The struts in each row desirably are arranged in a zig-zag or generally saw-tooth like pattern extending in the direction of the circumference of the frame as shown. Adjacent struts in the same row can be interconnected to one another as shown in FIGS. 1 and 5 to form an angle A, which desirably is between about 90 and 110 degrees, with about 100 degrees being a specific example. The selection of angle A between approximately 90 and 110 degrees optimizes the radial strength of frame 12 when expanded yet still permits the frame 12 to be evenly crimped and then expanded in the manner described below.

In the illustrated embodiment, pairs of adjacent circumferential struts in the same row are connected to each other by a respective, generally U-shaped crown structure, or crown portion, 26. Crown structures 26 each include a horizontal portion extending between and connecting the adjacent ends of the struts such that a gap 28 is defined between the adjacent ends and the crown structure connects the adjacent ends at a location offset from the strut's natural point of intersection. Crown structures 26 significantly reduce residual strains on the frame 12 at the location of struts 20, 22, 24 during crimping and expanding of the frame 20 in the manner described below. Each pair of struts 22 connected at a common crown structure 26 forms a cell with an adjacent pair of struts 24 in the row above. Each cell can be connected to an adjacent cell at a node 32. Each node 32 can be interconnected with the lower row of struts by a respective vertical (axial) strut 30 that is connected to and extends between a respective node 32 and a location on the lower row of struts 20 where two struts are connected at their ends opposite crown structures 26.

In certain embodiments, lower struts 20 have a greater thickness or diameter than upper struts 22, 24. In one implementation, for example, lower struts 20 have a thickness T (FIG. 9) of about 0.42 mm and upper struts 22, 24 have a thickness T of about 0.38 mm. Because there is only one row of lower struts 20 and two rows of upper struts 22, 24 in the illustrated configuration, enlargement of lower struts 20 with respect to upper struts 22, 24 enhances the radial strength of the frame at the lower area of the frame and allows for more uniform expansion of the frame.

FIG. 9 shows a flattened view of a 120-degree segment of frame 12 shown in FIG. 7, the segment comprising a portion of the frame extending between two posts 18. As shown, the frame segment has three columns 34 and three rows 36a, 36b, 36c of struts per segment. Each column 34 is defined by the adjoining pairs of struts 20, 22, 24 extending between two axially extending struts 18, 30. Frame 12 desirably is comprised of three 120-degree segments, with each segment being bounded by two posts 18. Accordingly, frame 12 in the illustrated embodiment includes 9 total columns per frame.

The number of columns and rows desirably is minimized to reduce the overall crimp profile of the valve, as further discussed below. The arrangement of FIGS. 7 and 9 typically is used for valves that are less than about 29 mm in diameter, and are most suitable for valves that are about 20-26 mm in diameter. In working examples of valves comprising frame 12, a 20-mm valve can be crimped to a diameter of about 17 Fr, a 23-mm valve can be crimped to a diameter of about 18 Fr and a 26-mm valve can be crimped to a diameter of about 19 Fr. For valves that are about 29 mm and larger in diameter, it may be desirable to add another row and column of struts.

Figure 8:
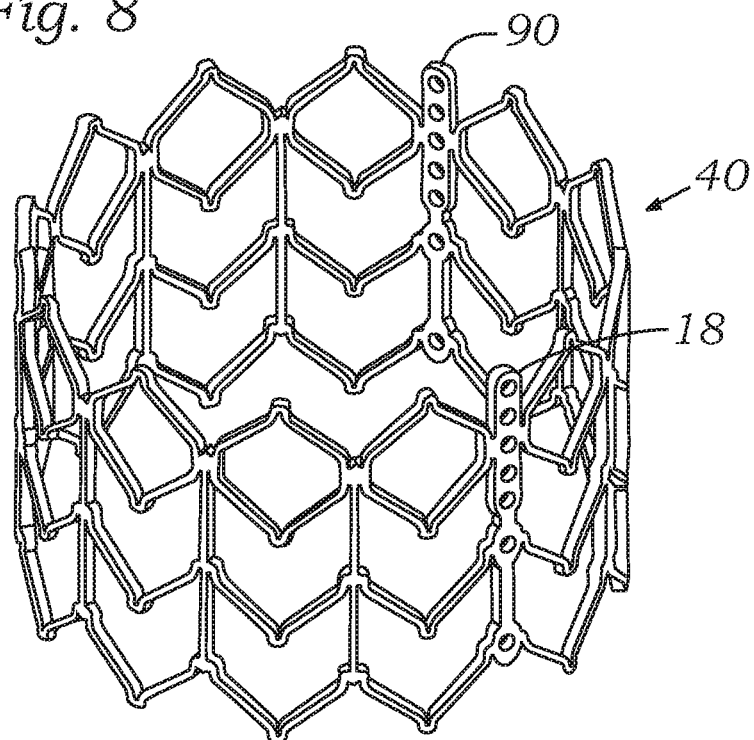
FIG. 8 is a perspective view of an alternative embodiment of a frame that can be used in the prosthetic valve of FIG. 1.

For example, FIGS. 8 and 10 show an alternative frame 40 that is similar to frame 12 except that frame 40 has four rows of struts (a lowermost, first row 52a of struts 42, a second row 52b of struts 44, a third row 52c of struts 46, and an uppermost row 52d of struts 48) instead of three rows of struts, as well as four columns 50 of struts for each 120-degree frame segment instead of three columns of struts. FIG. 10 shows a flattened view of a 120-degree segment of frame 40 shown in FIG. 8. Frame 40 in the illustrated embodiment includes three such 120-degree segments, providing 12 total columns 50 of struts for the frame.

Struts 46 of the third row desirably are facing in the opposite direction of the struts 48 of the fourth row (i.e., the apexes or crown portions are facing in the opposite direction), to help avoid buckling of the vertical posts of the frame during crimping and expansion of the valve. Struts 44 of the second row can be arranged so as to be facing in the same direction as the struts 42 of the first row as shown (i.e., the apexes or crown portions are facing in the same direction). Alternatively, struts 44 of the second row can be facing in the opposing direction from struts 42 of the first row so as to form square cells, like the cells formed by the struts 46, 48 of the third and fourth rows, respectively. Frame 40 can also include axially extending struts 54 connected to and extending between the ends of each strut 42, 44, 46, and 48 aligned in a column 50 that are not connected to a post 18. As noted above, frame 40 is most suitable for valves 29 mm and larger in diameter (when expanded to its functional size). In a working example of a valve incorporating frame 40, a 29-mm valve can be crimped to a diameter of about 21 Fr.

Suitable plastically-expandable materials that can be used to form the frame include, without limitation, stainless steel, a nickel based alloy (e.g., a nickel-cobalt-chromium alloy), polymers, or combinations thereof. In particular embodiments, frame 20 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 20 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring again to FIG. 1, skirt 16 can be formed, for example, of polyethylene terephthalate (PET) ribbon. The thickness of the skirt can vary, but is desirably less than 6 mil, and desirably less than 4 mil, and even more desirably about 2 mil. Skirt 16 can be secured to the inside of frame 12 via Lenzing sutures 56, as shown in FIG. 1. Leaflet structure 14 can be attached to the skirt via a thin PET reinforcing strip 68 (or sleeve), discussed below, which enables a secure suturing and protects the pericardial tissue of the leaflet structure from tears. Leaflet structure 14 can be sandwiched between skirt 16 and the thin PET strip 68 as shown. Suture 58, which secures the PET strip and the leaflet structure 14 to skirt 16 can be any suitable suture, such as an Ethibond suture. Suture 58 desirably tracks the curvature of the bottom edge of leaflet structure 14, as described in more detail below. Leaflet structure 14 can be formed of bovine pericardial tissue, biocompatible synthetic materials, or various other suitable natural or synthetic materials as known in the art and described in U.S. Pat. No. 6,730,118, which is incorporated by reference herein.

Figure 6:
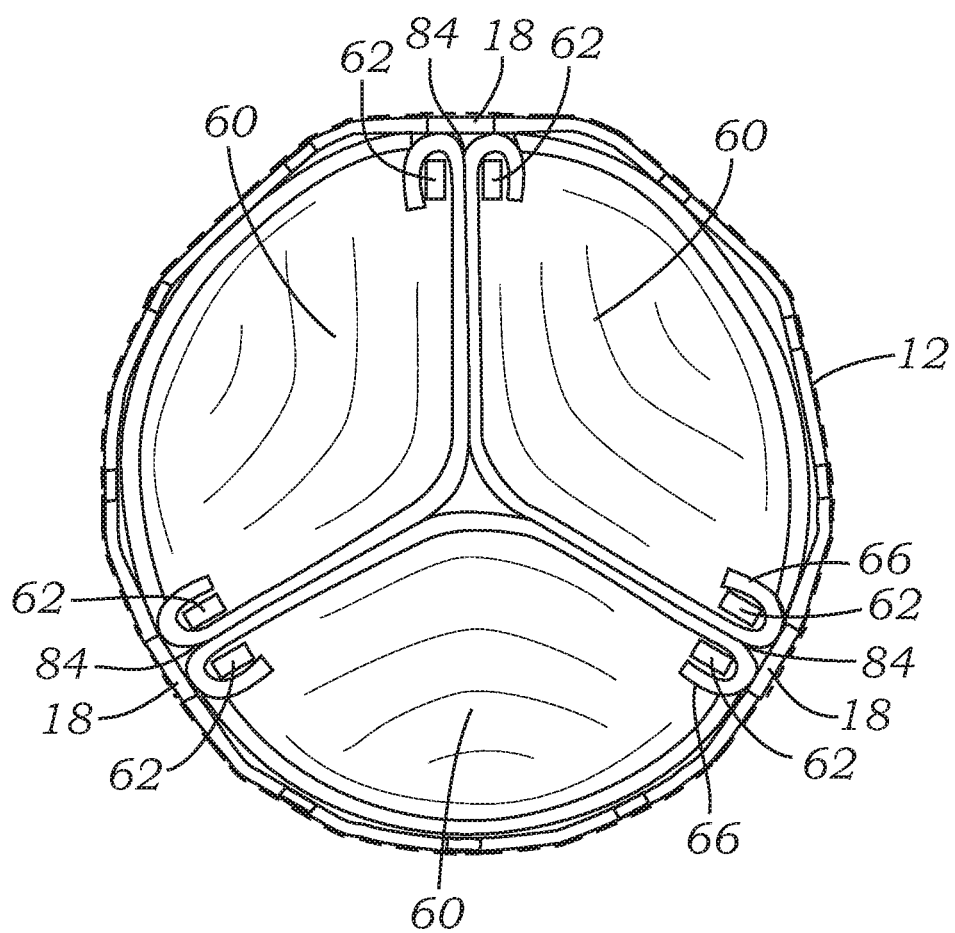
FIG. 6 is a top plan view of the prosthetic valve of FIG. 1.

Leaflet structure 14 can comprise three leaflets 60, which can be arranged to collapse in a tricuspid arrangement, as best shown in FIGS. 2 and 6. The lower edge of leaflet structure 14 desirably has an undulating, curved scalloped shape (suture line 58 shown in FIG. 1 tracks the scalloped shape of the leaflet structure). By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve.

Leaflets 60 can be secured to one another at their adjacent sides to form commissures 84 of the leaflet structure (the edges where the leaflets come together). Leaflet structure 14 can be secured to frame 12 using suitable techniques and mechanisms. For example, as best shown in FIG. 6, commissures 84 of the leaflet structure desirably are aligned with the support posts 18 and secured thereto using sutures. The point of attachment of the leaflets to the posts 18 can be reinforced with bars 62 (FIG. 11), which desirably are made of a relatively rigid material (compared to the leaflets), such as stainless steel.

Figure 12:
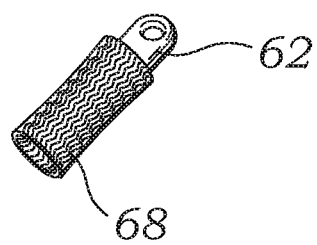
FIG. 12 is a perspective view of the reinforcing bar of FIG. 11 and a PET sleeve that can be used to cover the bar.
Figure 13:
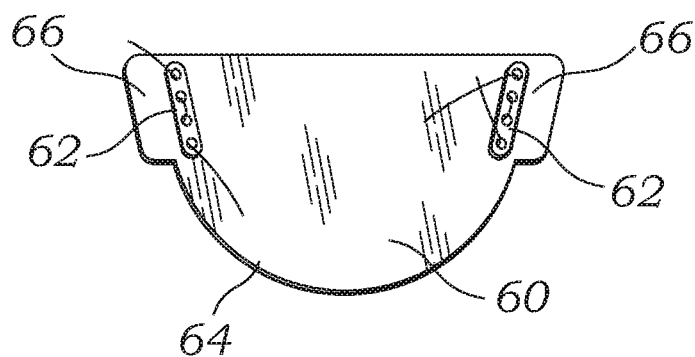
FIG. 13 is a flattened view of a leaflet of the valve shown in FIG. 1.
Figure 18:
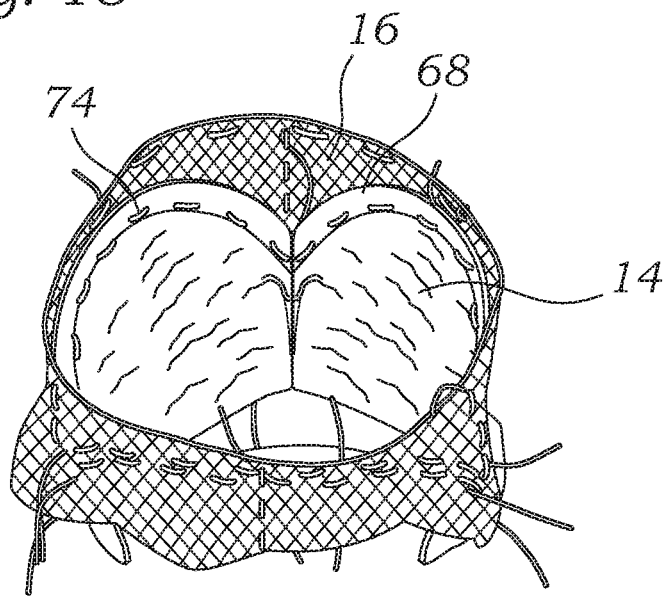
FIG. 18 is a bottom perspective view of the leaflet structure connected to the skirt so as to form a leaflet assembly.

FIG. 13 shows a single leaflet 60, which has a curved lower edge 64 and two flaps 66 extending between the upper edge and curved lower edge of the leaflet. The curved lower edge 64 forms a single scallop. When secured to two other leaflets to form leaflet structure 14, the curved lower edges of the leaflets collectively form the scalloped shaped lower edge portion of the leaflet structure (as best shown in FIG. 18). As further shown in FIG. 13, two reinforcing bars 62 can be secured to the leaflet adjacent to flaps 66 (e.g., using sutures). The flaps can then be folded over bars 62 and secured in the folded position using sutures. If desired, as shown in FIG. 12, each bar 62 can be placed in a protective sleeve 68 (e.g., a PET sleeve) before being secured to a leaflet.

Figure 14:
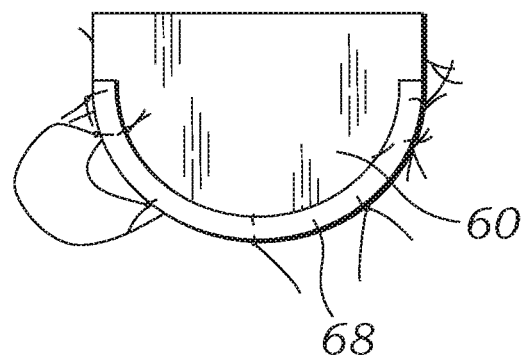
FIG. 14 is a flattened view of the opposite side of the leaflet showing a reinforcing strip secured adjacent the bottom edge of the leaflet.
Figure 15:
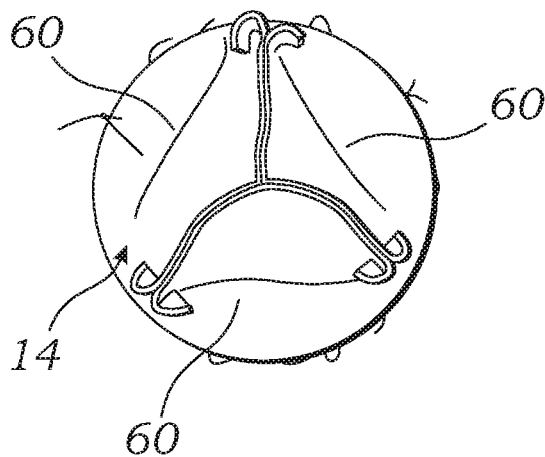
FIG. 15 is a top plan view of the leaflet structure of the valve of FIG. 1 prior to attachment to the frame.

As shown in FIG. 14, the lower curved edge 64 of the leaflet can be reinforced for later securement to the skirt 16, such as by securing a reinforcing strip 68 along the curved lower edge between flaps 66 on the side of the leaflet opposite bars 62. Three such leaflets 60 can be prepared in the same manner and then connected to each other at their flaps 66 in a tricuspid arrangement to form leaflet structure 14, as shown in FIG. 15. The reinforcing strips 68 on the leaflets collectively define a ribbon or sleeve that extends along the lower edge portion of the inside surface of the leaflet structure.

As noted above, leaflet structure 14 can be secured to frame 12 with skirt 16. Skirt 16 desirably comprises a tough, tear resistant material such as PET, although various other synthetic or natural materials can be used. Skirt 16 can be much thinner than traditional skirts. In one embodiment, for example, skirt 16 is a PET skirt having a thickness of about 0.07 mm at its edges and about 0.06 mm at its center. The thinner skirt can provide for better crimping performances while still providing good perivalvular sealing.

Figure 16:
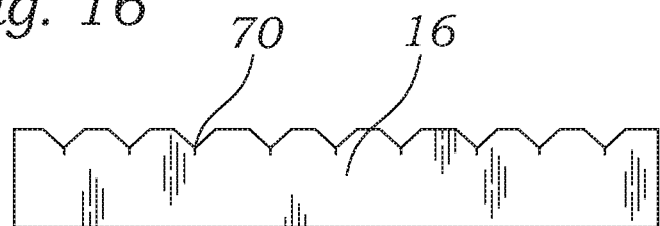
FIG. 16 is a flattened view of the skirt used in the valve shown in FIG. 1.
Figure 17:
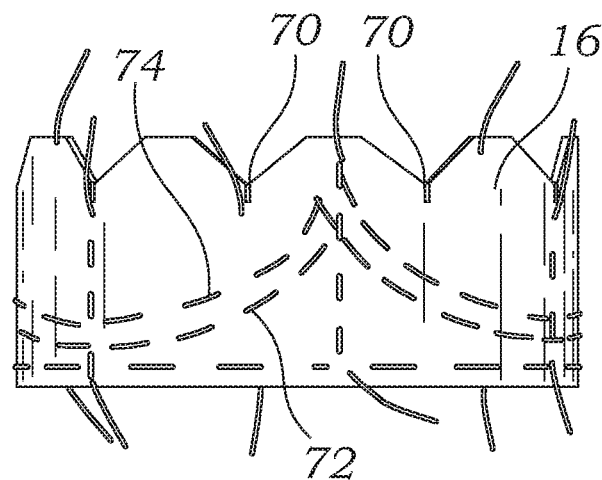
FIG. 17 is a side view of the skirt illustrating suture lines for attaching the skirt to the leaflet structure.

FIG. 16 shows a flattened view of the skirt before the opposite ends are secured to each other to form the annular shape shown in FIG. 17. As shown, the upper edge of skirt 16 desirably has an undulated shape that generally follows the shape of the second row of struts 22 of the frame. In this manner, the upper edge of skirt 16 can be tightly secured to struts 22 with sutures 56 (as best shown in FIG. 1). Skirt 16 can also be formed with slits 70 to facilitate attachment of the skirt to the frame. Slits 70 are aligned with crown structures 26 of struts 22 when the skirt is secured to the frame. Slits 70 are dimensioned so as to allow an upper edge portion of skirt to be partially wrapped around struts 22 and reduce stresses in the skirt during the attachment procedure. For example, in the illustrated embodiment, skirt 16 is placed on the inside of frame 12 and an upper edge portion of the skirt is wrapped around the upper surfaces of struts 22 and secured in place with sutures 56. Wrapping the upper edge portion of the skirt around struts 22 in this manner provides for a stronger and more durable attachment of the skirt to the frame. Although not shown, the lower edge of the skirt can be shaped to conform generally to the contour of the lowermost row of struts 22 to improve the flow of blood past the inflow end of the valve.

As further shown in FIG. 17, various suture lines can be added to the skirt to facilitate attachment of the skirt to the leaflet structure and to the frame. For example, a scalloped shaped suture line 72 can be used as a guide to suture the lower edge of the leaflet structure at the proper location against the inner surface of the skirt using suture 59 (as best shown in FIG. 5). Another scalloped shaped suture line 74 (FIG. 17) can be use as a guide to suture the leaflet structure to the skirt using sutures 58 (FIG. 1). Reinforcing strips 68 secured to the lower edge of the leaflets reinforces the leaflets along suture line 58 and protects against tearing of the leaflets. FIG. 18 shows a leaflet assembly comprised of skirt 16 and leaflet structure 14 secured to the skirt. The leaflet assembly can then be secured to frame 12 in the manner described below. In alternative embodiments, the skirt, without the leaflet structure, can be connected to the frame first, and then the leaflet structure can be connected to the skirt.

FIG. 6 shows a top view of the valve assembly attached to frame 12. Leaflets 60 are shown in a generally closed position. As shown, the commissures of the leaflets are aligned with posts 18 of the frame. The leaflets can be secured to the frame using sutures extending through flaps 66 of the leaflets, openings 76 in bars 62, and openings 78 in posts 18, effectively securing flaps 66 to posts 18. As noted above, bars 62 reinforce the flaps at the area of connection with posts and protect against tearing of the leaflets.

Figure 6A:
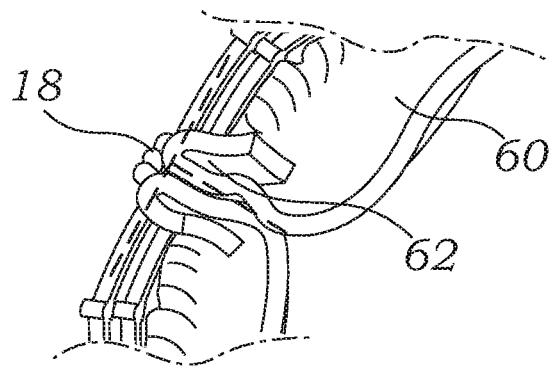
FIG. 6A is an enlarged partial top view of the valve of FIG. 1 illustrating the positioning of the reinforcing bars with respect to the commissure attachment posts of the frame.

As shown in FIG. 6A, bars 62 desirably are aligned perpendicular and as straight as possible with respect to posts 18 of the frame, such that bars 62 and post 18 at each commissure form a "T" shape. The width of bars 62 and the attachment of the commissures via the bars provides a clearance between the deflectable portions of the leaflets 60 (the portions not secured by sutures to the frame) and the frame, while the edge radius (thickness) of bars 62 serves as a flex hinge for the leaflets 60 during valve opening and closing, thereby increasing the space between the leaflets and the frame. By increasing the space between the moving portions of the leaflets and frame and by having the leaflets flex against an edge radius of bars 62, contact between the moving portions of the leaflets (especially the outflow edges of the leaflets) and the frame can be avoided during working cycles, which in turn improves the durability of the valve assembly. This configuration also enhances perfusion through the coronary sinuses.

Figure 19:
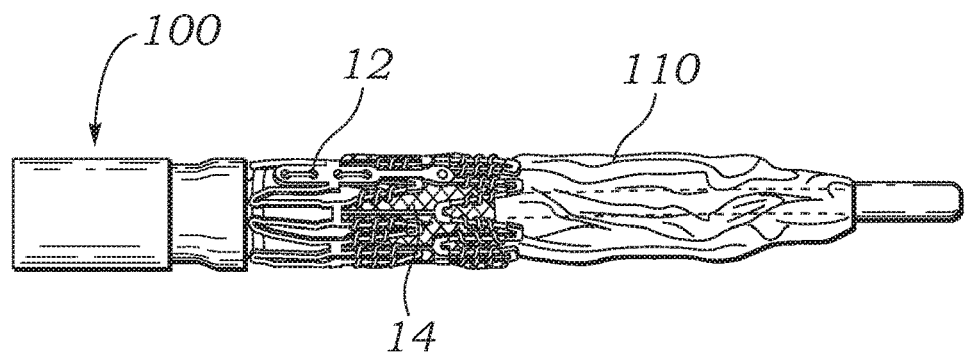
FIG. 19 is a side view of a balloon catheter and a prosthetic valve crimped onto the balloon of the balloon catheter.

FIG. 19 depicts a side view of a valve 10 crimped on a balloon delivery catheter 100. The valve is crimped onto balloon 110 of balloon catheter 100. It is desirable to protect leaflet structure 14 of the valve from damage during crimping to ensure durability of the leaflet structure and at the same time, it is desirable to reduce as much as possible the crimped profile size of the valve. During the crimping procedure the tissue of the leaflet structure (e.g., bovine pericardial tissue or other suitable tissue) is pressed against against the inner surface of the metal frame and portions of the tissue can protrude into the open cells of the frame between the struts and can be pinched due to the scissor-like motion of the struts of the frame. If the valve is severely crimped to achieve a small crimping size, this scissor-like motion can result in cuts and rupture of the tissue leaflets.

Skirt 16, described above, can protect against damage to the leaflet structure during crimping to a certain degree. However, the skirt's main purpose is structural and it does not in certain embodiments cover the entire frame. Therefore, in such embodiments, the skirt may not fully protect the leaflet structure during crimping and as such, the frame can still cause damage to the leaflet structure.

Figure 20:
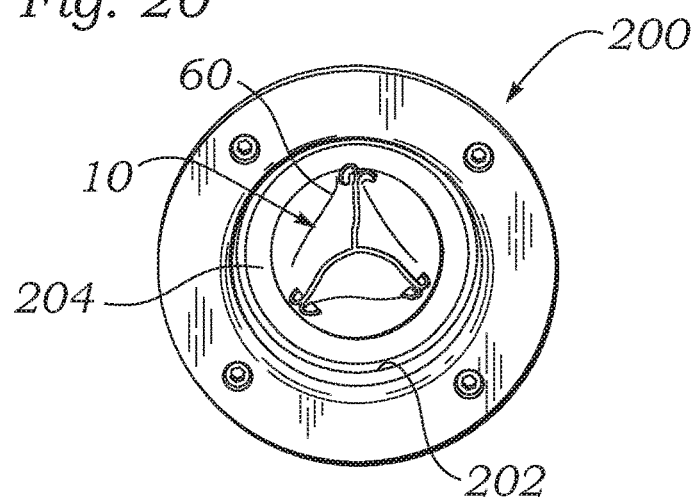
FIG. 20 is a front view of a crimping device showing a prosthetic valve positioned in the crimping aperture of the crimping device with a protective sleeve disposed between the valve and the crimping jaws.
Figure 21:
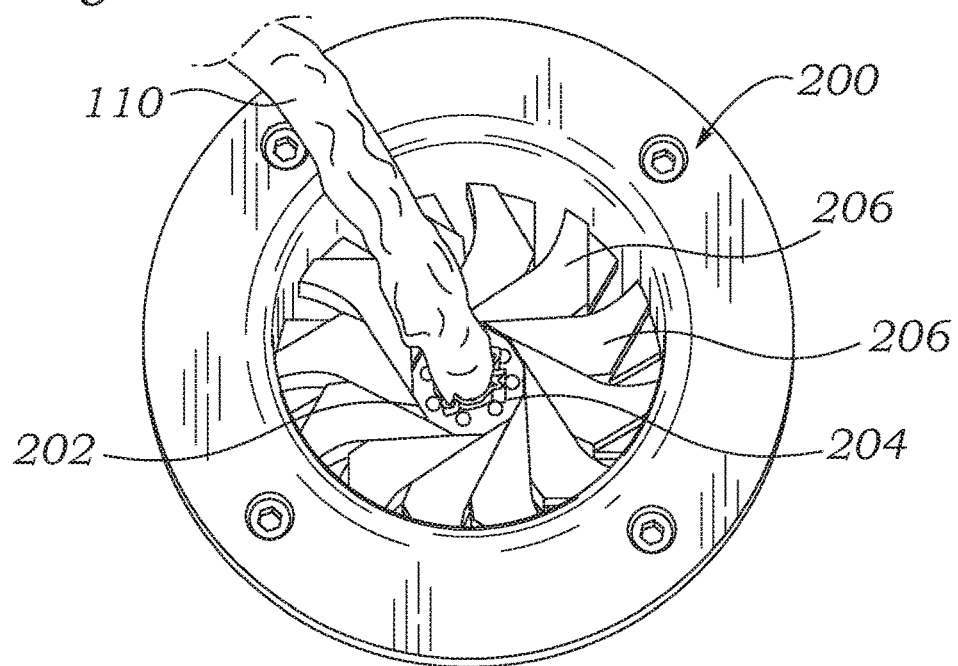
FIG. 21 is a front view of the crimping device shown after the crimping jaws are forced inwardly to compress the valve and the protective sleeve.
Figure 22:
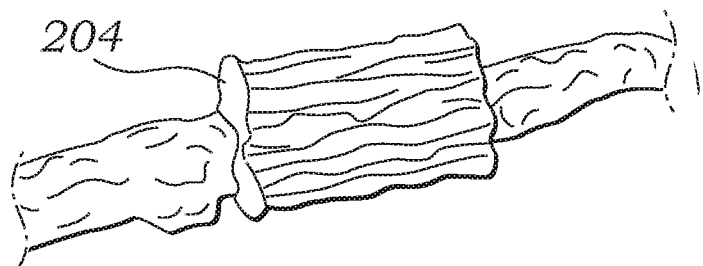
FIG. 22 is a side view of the valve and protective sleeve after removal from the crimping device.

FIGS. 20 and 21 show an embodiment of a crimping apparatus for atraumatic crimping of a valve onto a balloon in a manner that further protects against damage to the leaflets. The crimping apparatus (also referred to as a crimper), indicated generally at 200, has an aperture 202 sized to receive a valve in an expanded state. FIG. 20 shows aperture 202 in a fully open or dilated state with a valve 10 positioned inside aperture 202. Crimping apparatus 200 has a plurality of crimper jaws 206 (12 in the illustrated embodiment) which are configured to move radially inwardly to radially compress (crimp) the valve to a smaller profile around the balloon of a balloon catheter.

A deformable material is positioned between the outside of the frame and the crimping jaws 206. In the illustrated embodiment, the deformable material comprises a protective sleeve, or covering, 204 that is placed around the valve so that it covers the outer surface of the frame of the valve and prevents the hard surface of the crimping jaws from directly contacting the frame of the valve. The sleeve 204 desirably is sized to fully cover the outer surface of the frame. Sleeve 204 desirably is made of a soft, flexible and compressible material. The sleeve can be formed from generally available materials, including, but not limited to, natural or synthetic sponge (e.g., polyurethane sponge), a foamed material made of a suitable polymer such as polyurethane or polyethylene, or any of various suitable elastomeric materials, such as polyurethane, silicon, polyolefins or a variety of hydrogels, to name a few.

The sleeve is desirably stored in a wet environment (e.g., immersed in saline) prior to use. After placing sleeve 204 around the valve, the valve and the sleeve are placed into crimping apparatus 200 as shown in FIG. 20. Balloon 110 of a balloon catheter can then be positioned within the leaflets 60 of the valve (FIG. 21). FIG. 21 shows crimper jaws 206 surrounding sleeve 204, which in turn surrounds frame 12 and leaflet structure 14 of valve 10. Balloon 110 typically is placed at the center of the valve so that the valve can be evenly expanded during implantation of the valve within the body.

As seen in FIG. 21, during crimping, the sponge-like material of protective sleeve 204 protrudes into the open cells of frame 12 and occupies this space, thereby preventing leaflet structure 14 from entering this space and being pinched or otherwise damaged. After crimping is completed, the valve with the protective sleeve is removed from the crimping apparatus. Sleeve 204 can then be gently peeled away from the frame. Because the protective sleeve presses the leaflet structure inwardly and away from the frame during crimping, the valve can be crimped to a small profile without damaging the leaflet structure.

Figure 23:
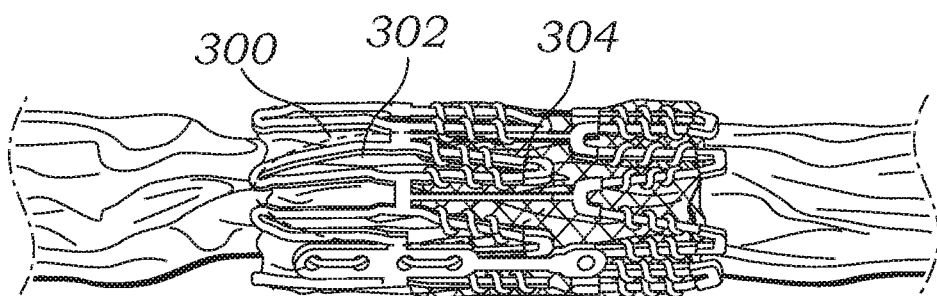
FIG. 23 is a side view of a prosthetic valve that has been crimped onto a balloon of a balloon catheter without a protective sleeve.
Figure 24:
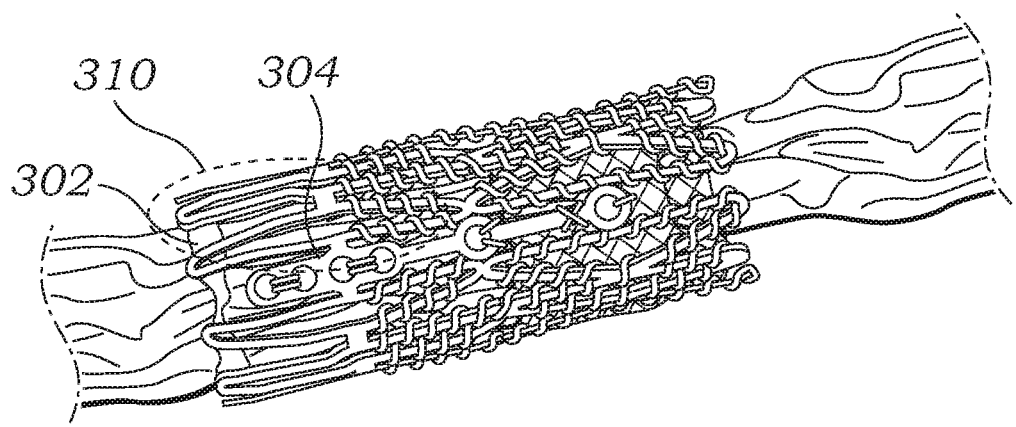
FIG. 24 is a side view of a prosthetic valve that has been crimped onto a balloon of a balloon catheter using a protective sleeve in the manner shown in FIGS. 20-21.

FIGS. 23 and 24 illustrate an advantage that can be gained by using protective sleeve 204. FIG. 23 shows a prosthetic valve that was crimped without using the protective sleeve. Dotted line 300 identifies an area of the valve where leaflet structure 302 has been pressed between struts of a frame 304, which can damage the leaflet structure as discussed above.

In contrast, FIG. 24 shows a prosthetic valve that was crimped using protective sleeve 204. In this example, leaflet structure 302 was pressed inwardly and away from the inside of frame 304 and, therefore, the leaflet structure was not pinched or squeezed between the struts of the frame.

Accordingly, since the leaflet structure is pushed away from the frame when the protective sleeve is used, the leaflet structure is less likely to be pinched or cut during the crimping process. Also, when using a protective sleeve, a very ordered structure of balloon-leaflets-frame (from inward to outward) can be achieved. When no such protective sleeve is utilized, some portion of the balloon, leaflets, and frame are much more likely to overlap after the crimping procedure and the resulting structure is less predictable and uniform.

In addition to the foam or sponge-type protective sleeve described above, other types of sleeves or protective layers of deformable material can be used to protect the leaflets against damage during crimping of a valve. In one implementation, for example, a layer (e.g., rectangular slices) of deformable material (e.g., sponge, rubber, silicon, polyurethane, etc.) can be disposed on each crimping jaw 206 so as to form a sleeve around the valve upon crimping. Alternatively, deformable packets filled with a flowable, deformable material, such as a gel or gas, can be disposed on each crimping jaw for contacting the valve upon crimping. In addition, the deformable material (e.g., sleeve 204) can be covered with a thin PET cloth, among many other fabric materials or other suitable materials, to prevent particles of the deformable materials from migrating to the valve during crimping.

The skirt of a prosthetic valve serves several functions. In particular embodiments, for example, the skirt functions to seal and prevent (or decrease) perivalvular leakage, to anchor the leaflet structure to the frame, and to protect the leaflets against damage caused by contact with the frame during crimping and during working cycles of the valve. The skirt used with the prosthetic valve discussed above has been described as being a fabric, such as a PET cloth. PET or other fabrics are substantially non-elastic (i.e., substantially non-stretchable and non-compressible). As such, the skirt in certain implementations limits the smallest achievable crimping diameter of the valve and can wrinkle after expansion from the crimped diameter.

In alternative embodiments, such as discussed below, a prosthetic valve can be provided with a skirt that is made of a stretchable and/or compressible material, such as silicon. Due to the compressibility of such a skirt, the valve can be crimped to a relatively smaller diameter as compared to a valve having a non-compressible skirt. Furthermore, such a skirt can recover its original, smooth surfaces with little or no wrinkling after expansion from the crimped state.

Figure 25:
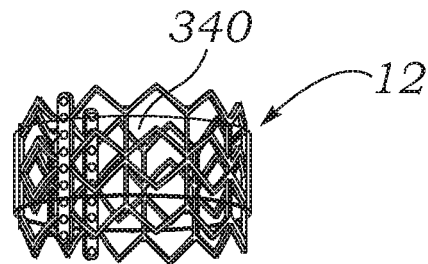
FIG. 25 is a side view of a frame for a prosthetic valve having a silicon skirt, or sleeve, disposed on the outside of the frame.

FIG. 25 shows an embodiment of a frame 12 that has an elastic "over-tube" skirt or sleeve 340 that extends completely around and covers at least a portion of the outside of the frame. In particular embodiments, skirt 340 is made of silicon, which can undergo large deformations while maintaining its elasticity. Such a silicon skirt can be a thin sleeve that covers a portion of frame 12 from the outside. In the illustrated embodiment, the height of the skirt is less than the overall height of frame 12, however, the skirt can vary in height and need not be the height shown in FIG. 25. For example, the height of the skirt can be the same as or greater than that of the frame so as to completely cover the outside of the frame. In an alternative embodiment, the skirt 340 can be mounted to the inside of the frame using, for example, sutures or an adhesive. When mounted inside of the frame, the skirt can protect the leaflets from abrasion against the inside of the frame. Other materials that can be used to form the skirt or sleeve include, but are not limited to, PTFE, ePTFE, polyurethane, polyolefins, hydrogels, biological materials (e.g., pericardium or biological polymers such as collagen, gelatin, or hyaluronic acid derivatives) or combinations thereof.

Figure 26:
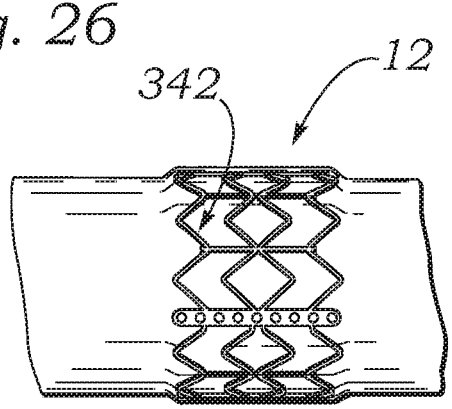
FIG. 26 is a side view of a frame for a prosthetic valve having a silicon encapsulating layer covering the inside and outside of the frame.

In another embodiment, the entire frame or a portion thereof can be dipped in liquefied material (e.g., liquid silicon or any of the materials described above for forming the sleeve 340 that can be liquefied for dip coating the frame) in order to encapsulate the entire frame (or at least that portion that is dipped) in silicon. FIG. 26 is a side view of a frame 12 that has been dipped in silicon to form a continuous cylindrical silicon covering 342 encapsulating the struts of the frame and filling the spaces between the struts. FIG. 26 shows the covering 342 before it is trimmed to remove excess material extending beyond the ends of the frame. Although less desirable, the frame can be dipped such that the silicon encapsulates the struts of the frame but does not fill the open spaces between the struts of the frame.

Figure 27:
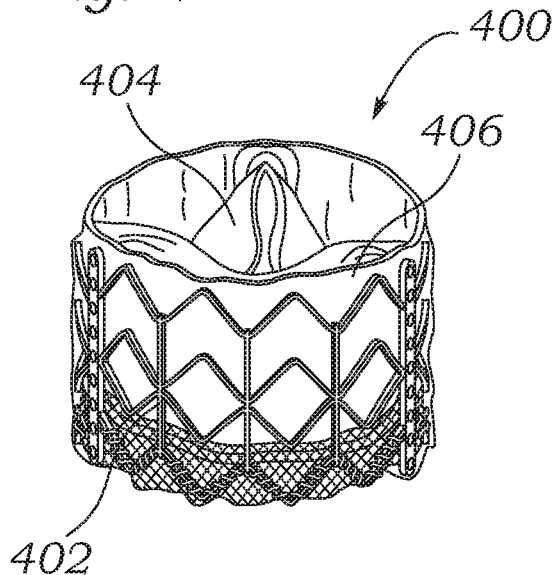
FIG. 27 is a perspective view of a prosthetic valve comprising a frame having a silicon encapsulating layer.
Figure 28:
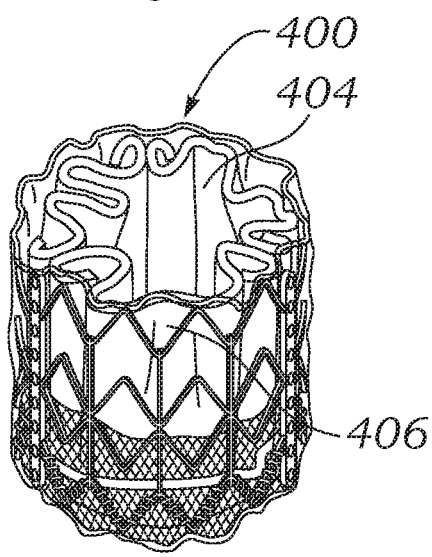
FIG. 28 is a perspective view of the valve of FIG. 27 after it has been crimped to a smaller diameter.
Figure 29:
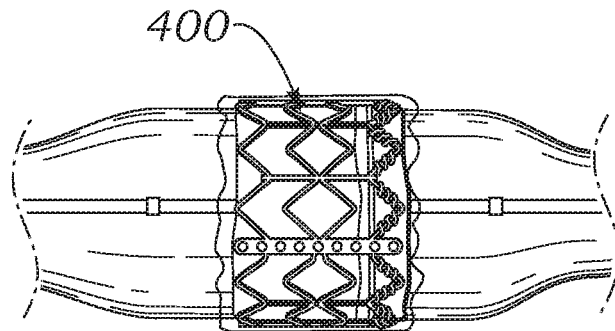
FIG. 29 is a side view of the valve of FIG. 27 after it has been expanded by a balloon catheter.

FIG. 27 shows an embodiment of a prosthetic valve 400 comprising a frame 402 and a leaflet structure 404 mounted to the inside of the frame (e.g., using sutures as shown). Frame 402 has a skirt in the form of silicon covering 406 that is formed, for example, by dipping the frame into liquid silicon. FIG. 27 shows valve 400 in its expanded state. In FIG. 28, valve 400 has been crimped to a smaller profile. During crimping, coating 406, which extends across and fills the open cells between the struts of the frame, is effective to push leaflet structure 404 inward and away from the frame, thereby protecting the leaflet structure from pinching or tearing. FIG. 29 shows valve 400 after being expanded by a balloon of a balloon catheter.

Figure 30A:
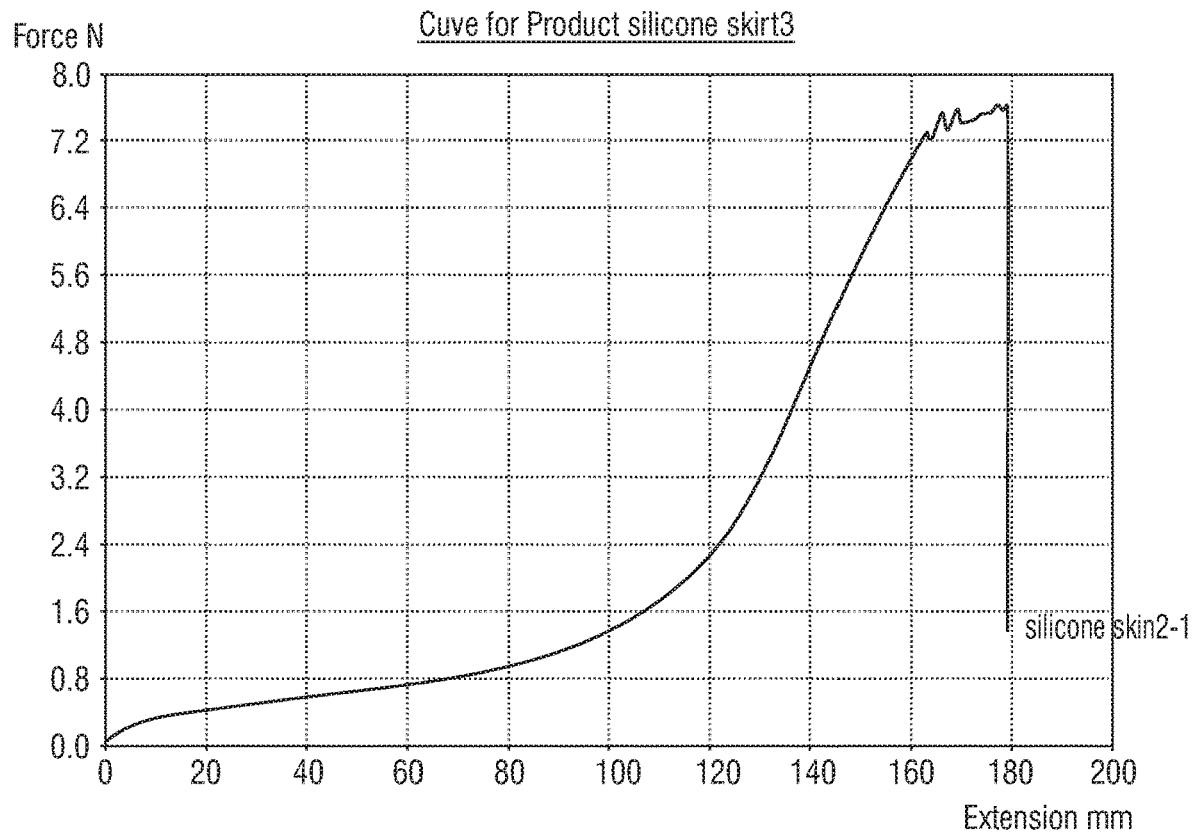
FIGS. 30A-30C are graphs illustrating the results of respective uniaxial tests performed on respective silicon test strips.
Figure 30B:
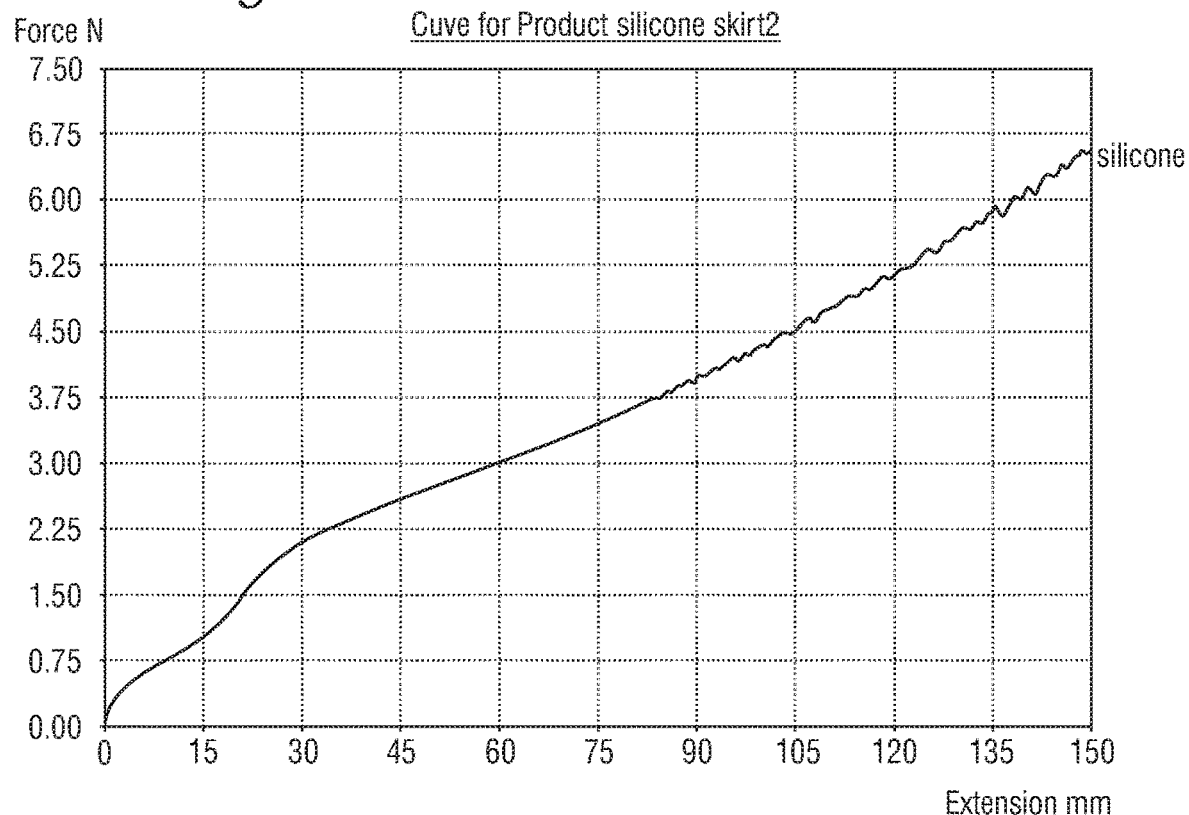
Figure 30C:
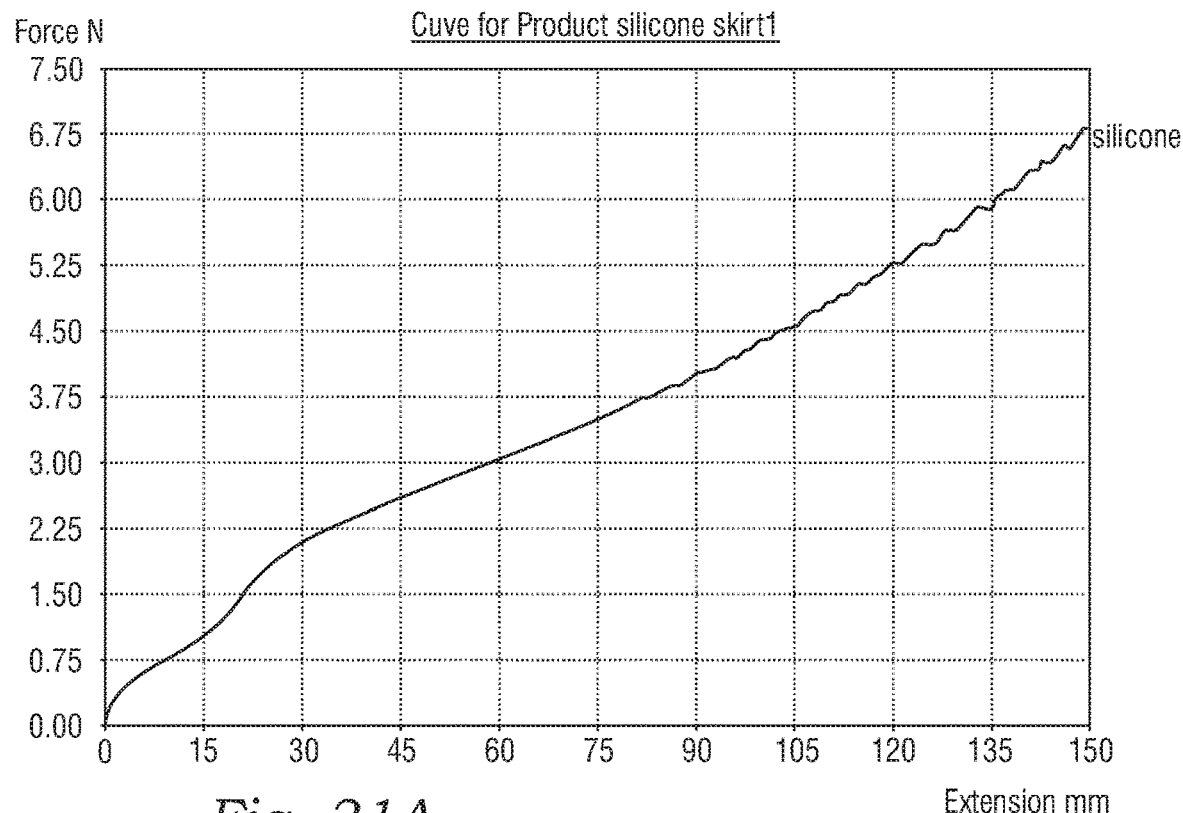
Figure 31A:
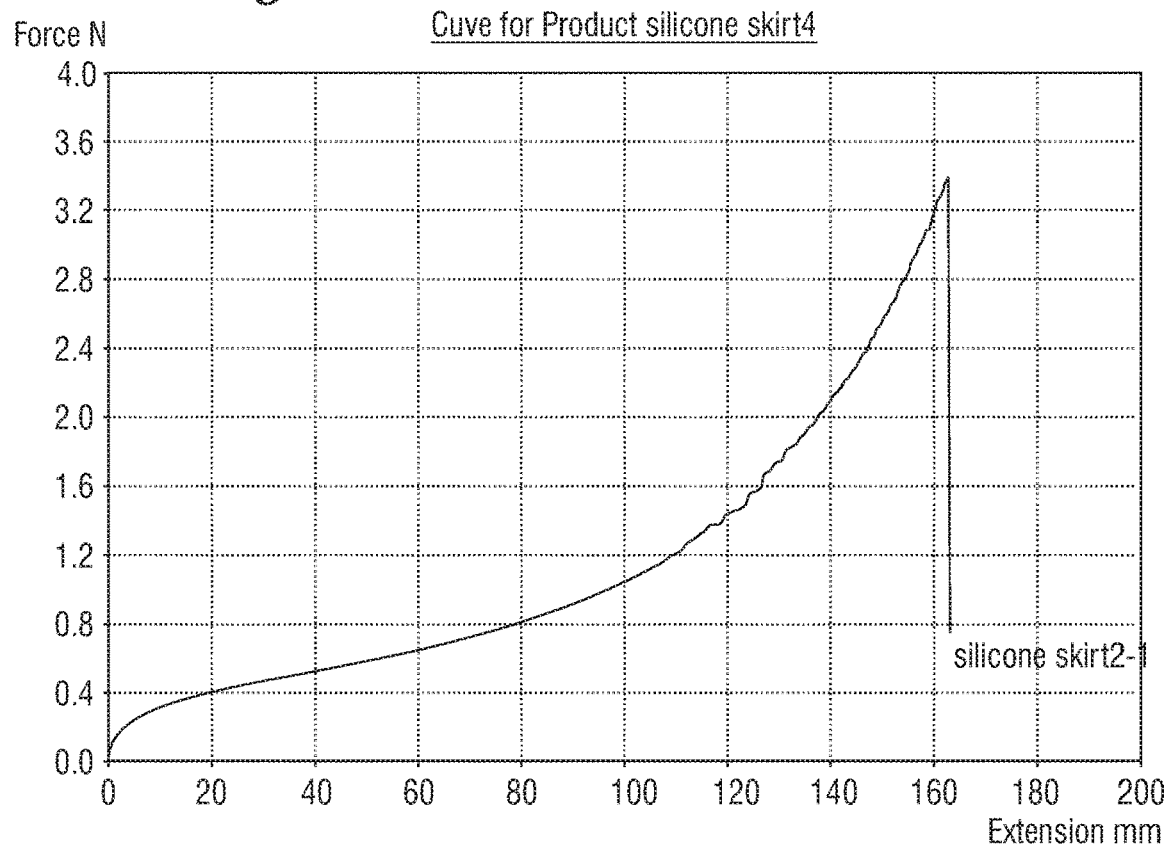
Figure 31B:
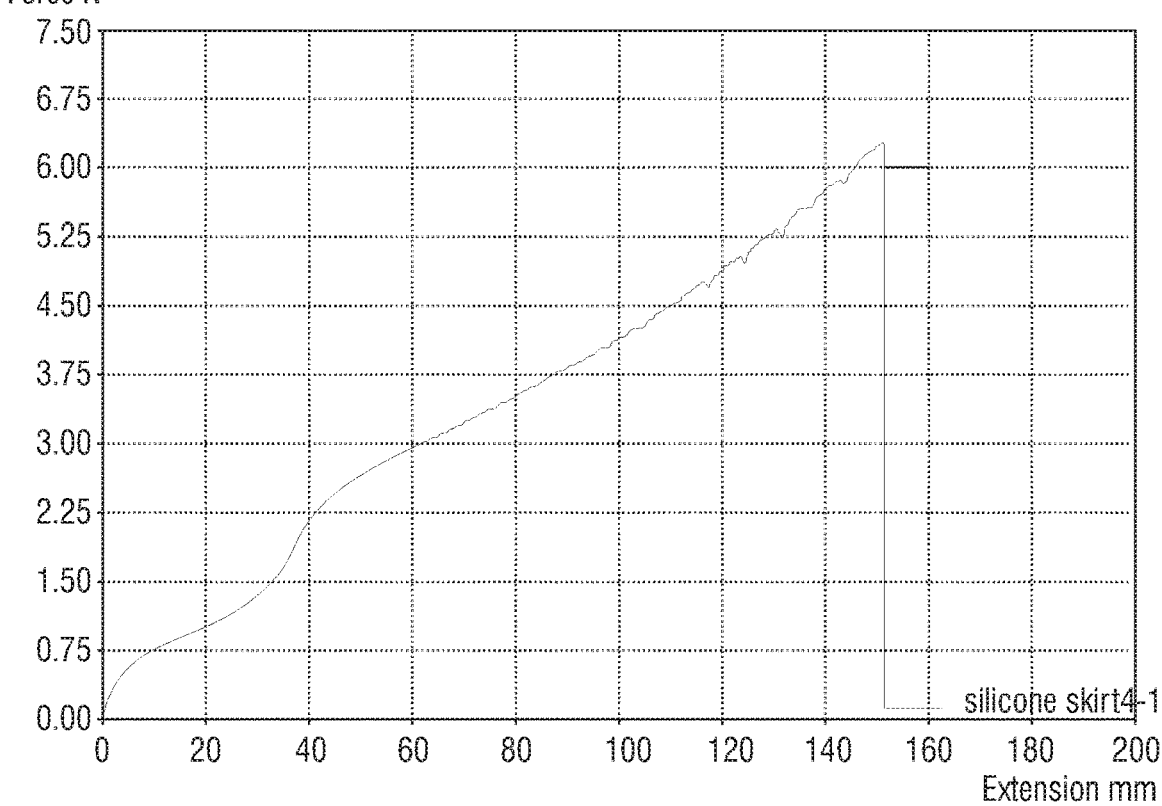
Figure 31C:
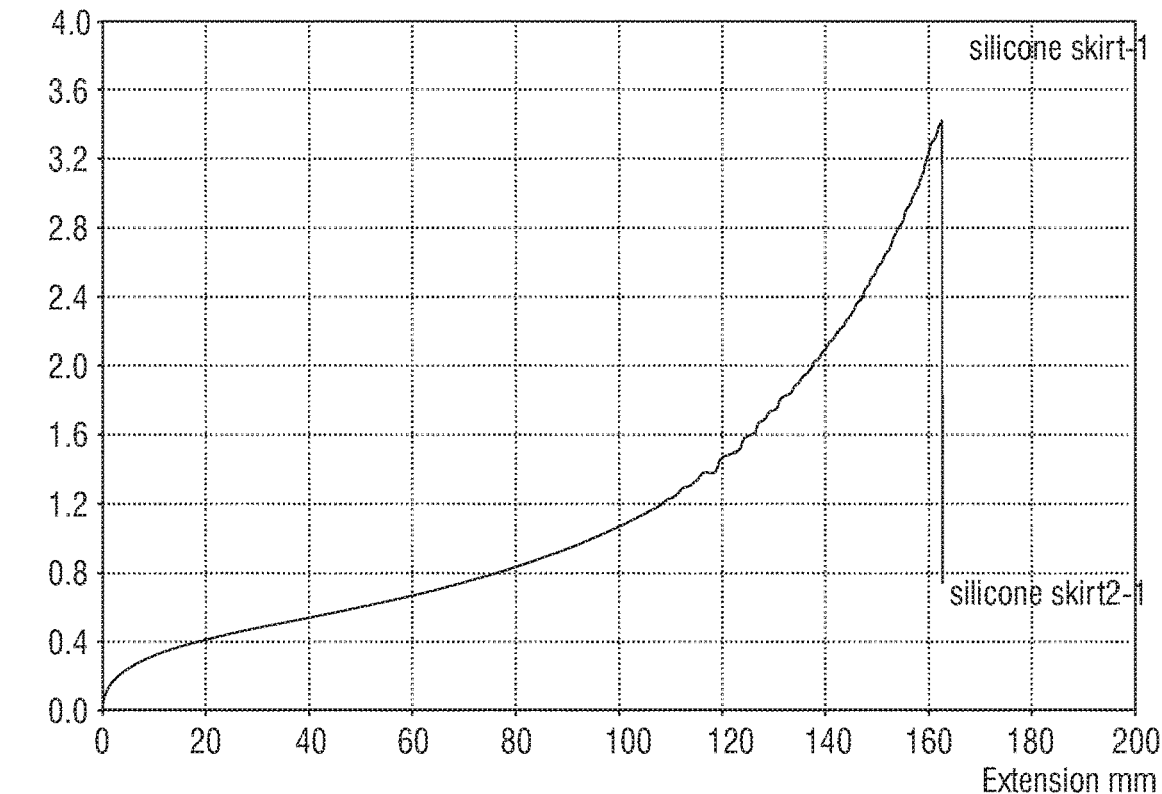

In order to test the durability and stretch resistance of the silicon used, several uniaxial tests were conducted. In particular, silicon strips of about 5×50 mm (with a thickness of about 0.85 mm) were tested in a uniaxial tester. FIGS. 30A-30C show graphs of the results of the uniaxial testing of silicon strips. In addition, tears were deliberately introduced into silicon strips at a middle of the strips and at the edge of the strips while the strips were stretched on a uniaxial tester. The tears were introduced by making holes in the silicon strips with a needle. FIGS. 31A-31F show graphs of the results of the uniaxial testing of silicon strips with deliberately introduced tears.

It was found that ultimate tensile stretch for a thin layer of silicon was over 500% and that samples that had tears that were deliberately introduced continued to show notable strength. Accordingly, the elasticity of silicon permits silicon dipped frames to be crimped to very low profiles and expanded back out to larger profiles without significant damage to the silicon layer. In addition, the silicon material can increase friction between the frame and the native annulus where the prosthetic valve is implanted, resulting in better anchoring and preventing/reducing perivalvular leaks.

A silicon skirt can be mounted on a frame by various means, including by using a mandrel. Also, it may be desirable to use a silicon skirt in combination with a cloth or fabric skirt. For example, it may be desirable to place a silicon skirt on the outside of a cloth or fabric skirt that is surrounding at least a portion of a frame.

Alternatively or additionally, a silicon skirt could also be placed on the inside of the frame and attached to the frame so that it offers the leaflets improved protecting during working cycles. Alternatively, instead of silicon, the skirt can be made of an auxetic and/or swelling material, such as synthetic or natural hydrogels. An auxetic material is one that expands laterally while stretched longitudinally, which means that this material has a negative Poisson ration. If the frame is covered with an auxetic material it can expand radially while being stretched circumferentially when the valve is expanded from its crimped state. Such expansion can improve the fit of the valve at the native valve annulus, thereby preventing or reducing perivalvular leakage.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An assembly comprising:
  a delivery catheter comprising a balloon; and
  an implantable prosthetic heart valve that is radially collapsible to a collapsed configuration and radially expandable to an expanded configuration, the prosthetic heart valve comprising:
  a radially collapsible and expandable annular frame, the frame having three commissure attachment posts and at least three rows of circumferential struts including a first row of circumferential struts defining an inflow end of the frame and second and third rows of circumferential struts spaced apart from the first row adjacent an outflow end of the frame, each row of circumferential struts comprising angled struts arranged in a zig-zag pattern defining a plurality of crowns;
  a leaflet structure comprising three leaflets formed of pericardial tissue, each leaflet having an upper edge, a curved lower edge and two side flaps, wherein each side flap is secured to an adjacent side flap of another leaflet to form commissures of the leaflet structure, each commissure being sutured to one of the commissure attachment posts via sutures extending through apertures in the commissure attachment posts, wherein all of the apertures are located along the length of the frame between a first plane that is perpendicular to the length and defined by the crowns of the second row of circumferential struts and a second plane that is perpendicular to the length and defined by the crowns of the third row of circumferential struts; and an annular skirt secured to the inside of the annular frame and to the leaflet structure, the curved lower edge of each leaflet sutured to an inner surface of the skirt;

wherein the collapsed prosthetic heart valve can be mounted around the balloon and radially expanded to the expanded configuration with the balloon inside a patient's body.

2. The assembly of claim 1, wherein the prosthetic heart valve further comprises a reinforcing strip, separate from the annular skirt member, secured to an inner surface of the leaflet structure adjacent its curved lower edge such that the leaflets are sandwiched between the annular skirt member and the reinforcing strip.

3. The assembly of claim 1, wherein the crowns comprise U-shaped crown structures that interconnect adjacent ends of two angled struts, wherein the U-shaped crown structure comprises a first portion connected to and extending at a non-zero angle from the end of one of the struts, a second portion connected to and extending at a non-zero angle from the adjacent end of the other strut, and a third, intermediate portion extending between and connecting the first and second portions such that a gap is defined between the first and second portions and the adjacent ends of the struts.

4. The assembly of claim 1, wherein the skirt member has an upper edge and a lower edge, the upper edge being sutured to each strut of the second row of struts, and the lower edge being sutured to each strut of the first row of struts.

5. The assembly of claim 4, wherein the upper edge of the skirt is shaped to correspond to the zig-zag pattern of the second row of struts.

6. The assembly of claim 4, wherein each strut of the second row of struts is sutured to the upper edge of the skirt with a suture comprising a plurality of suture loops extending around the strut and through the upper edge of the skirt.

7. The assembly of claim 1, wherein the second and third row of struts define a row of cells defining openings in the frame along an outflow portion of the frame and wherein the skirt member covers an entire extent of an inner surface of the frame except for the openings in the row of cells.

8. The assembly of claim 1, wherein the frame is made of a plastically-expandable material.

9. The assembly of claim 8, wherein the plastically-expandable material comprises a nickel cobalt chromium alloy.

10. The assembly of claim 1, wherein each commissure attachment post is connected to adjacent ends of two struts of the second row of struts at a junction and extends from the junction toward the outflow end of the frame.

11. The assembly of claim 10, wherein each commissure attachment post includes apertures located downstream of the junction.

12. The assembly of claim 11, wherein each commissure attachment post includes an aperture located upstream of the junction.

13. An assembly comprising:
a delivery catheter comprising a balloon; and
an implantable prosthetic heart valve that is radially collapsible to a collapsed configuration and radially expandable to an expanded configuration, the prosthetic heart valve comprising:

a radially collapsible and expandable annular frame, the frame having three commissure attachment posts and at least three rows of circumferential struts including a first row of circumferential struts defining an inflow end of the frame, a second row of circumferential struts downstream of the first row, and a third row of circumferential struts spaced downstream of the second row and defining an outflow end of the frame, each row of circumferential struts comprising angled struts arranged in a zig-zag pattern, wherein the second and third row of struts define a row of cells defining openings in the frame along an outflow portion of the frame;

a leaflet structure comprising three leaflets forming three commissures of the leaflet structure, each commissure being connected to one of the commissure attachment posts only at locations along the commissure attachment posts between the outflow end of the frame and an upstream end of the row of cells; and an annular outer skirt extending around an outer surface of the frame;

wherein the collapsed prosthetic heart valve can be mounted around the balloon and radially expanded to the expanded configuration with the balloon inside a patient's body;

wherein the first row of struts forms exactly twelve crowns at the inflow end of the frame.

14. The assembly of claim 13, wherein the frame further comprises a fourth row of circumferential struts downstream of the first row and upstream of the second row.

15. The assembly of claim 14, wherein the row of cells defined between the second and third row of struts is a first row of cells, the second row of struts and the fourth row of struts define a second row of cells upstream of the first row of cells, and the fourth row of struts and the first row of struts define a third row of cells upstream of the second row of cells.

16. The assembly of claim 13, wherein each commissure attachment post is connected to adjacent ends of two struts of the second row of struts at a junction and extends from the junction toward the outflow end of the frame.

17. An assembly comprising:
a delivery catheter comprising a balloon; and
an implantable prosthetic heart valve that is radially collapsible to a collapsed configuration and radially expandable to an expanded configuration, the prosthetic heart valve comprising:

a radially collapsible and expandable annular frame, the frame having three commissure attachment posts and at least three rows of circumferential struts including a first row of circumferential struts defining an inflow end of the frame, a second row of circumferential struts downstream of the first row, and a third row of circumferential struts spaced downstream of the second row and defining an outflow end of the frame, each row of circumferential struts comprising angled struts arranged in a zig-zag pattern, wherein the second and third row of struts define a row of cells defining openings in the frame along an outflow portion of the frame;

a leaflet structure comprising three leaflets forming three commissures of the leaflet structure, each commissure being connected to one of the commissure attachment posts only at locations along the commissure attachment posts between the outflow end of the frame and a lower end of the row of cells; and an annular outer skirt extending around an outer surface of the frame;

wherein the collapsed prosthetic heart valve can be mounted around the balloon and radially expanded to the expanded configuration with the balloon inside a patient's body;

wherein each commis sure attachment post is connected to adjacent ends of two struts of the second row of struts at a junction and extends from the junction toward the outflow end of the frame;

wherein the commis sure attachment posts have cantilevered ends adjacent the outflow end of the frame.

18. An assembly comprising:

a delivery catheter comprising a balloon; and an implantable prosthetic heart valve that is radially collapsible to a collapsed configuration and radially expandable to an expanded configuration, the prosthetic heart valve comprising:

a radially collapsible and expandable annular frame, the frame having three commissure attachment posts and at least three rows of circumferential struts including a first row of circumferential struts defining an inflow end of the frame, a second row of circumferential struts downstream of the first row, and a third row of circumferential struts spaced downstream of the second row and defining an outflow end of the frame, each row of circumferential struts comprising angled struts arranged in a zig-zag pattern, wherein the second and third row of struts define a row of cells defining openings in the frame along an outflow portion of the frame;

a leaflet structure comprising three leaflets forming three commissures of the leaflet structure, each commis sure being connected to one of the commis sure attachment posts only at locations along the commis sure attachment posts between the outflow end of the frame and a lower end of the row of cells; and an annular outer skirt extending around an outer surface of the frame;

wherein the collapsed prosthetic heart valve can be mounted around the balloon and radially expanded to the expanded configuration with the balloon inside a patient's body;

wherein each commissure is connected to one of the commissure attachment posts with sutures only at locations along the commissure attachment posts between the outflow end of the frame and the lower end of the row of cells.

19. The assembly of claim 18, wherein the sutures extend through the commissures and openings in the commissure attachment posts.

20. An assembly comprising:

a delivery catheter comprising a balloon; and an implantable prosthetic heart valve that is radially collapsible to a collapsed configuration and radially expandable to an expanded configuration, the prosthetic heart valve comprising:

a radially collapsible and expandable annular frame, the frame having three commissure attachment posts and four rows of circumferential struts including a first row of circumferential struts, a second row of circumferential struts downstream of the first row, a third row of circumferential struts downstream of the second row, and a fourth row of circumferential struts downstream of the third row and defining an outflow end of the frame, each row of circumferential struts comprising angled struts arranged in a zig-zag pattern, wherein the third and fourth row of struts define a row of cells defining openings in the frame along an outflow portion of the frame, wherein the first row of struts includes exactly twelve crowns at the inflow end of the frame;

a leaflet structure comprising three leaflets forming three commissures of the leaflet structure, each commis sure being connected to one of the commis sure attachment posts only at locations along the commissure attachment posts between a first plane that is perpendicular to a longitudinal axis of the frame and intersects crowns of the third row of struts and a second plane that is perpendicular to the longitudinal axis and intersects crowns of the fourth row of struts; and an annular outer skirt extending around an outer surface of the frame;

wherein the collapsed prosthetic heart valve can be mounted around the balloon and radially expanded to the expanded configuration with the balloon inside a patient's body.

21. The assembly of claim 20, wherein each commissure attachment post is connected to adjacent ends of two struts of the third row of struts at a junction and extends from the junction toward the outflow end of the frame.

22. The assembly of claim 21, wherein the commissure attachment posts have cantilevered ends adjacent the outflow end of the frame.

23. The assembly of claim 22, wherein each commis sure is connected to one of the commissure attachment posts with sutures only at locations along the commis sure attachment posts between the junctions and the cantilevered ends of the commissure attachment posts.

24. The assembly of claim 23, wherein the sutures extend through the commissures and openings in the commissure attachment posts.

* * * * *